(12) United States Patent
Kubo et al.

(10) Patent No.: US 9,833,493 B2
(45) Date of Patent: Dec. 5, 2017

(54) METHOD FOR ACTIVATING HELPER T CELL

(71) Applicants: OTSUKA PHARMACEUTICAL CO., LTD., Tokyo (JP); INTERNATIONAL INSTITUTE OF CANCER IMMUNOLOGY, INC., Osaka (JP)

(72) Inventors: Hiroshi Kubo, Tokushima (JP); Shinji Sogo, Tokushima (JP); Haruo Sugiyama, Minoo (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 0 days.

(21) Appl. No.: 14/652,298

(22) PCT Filed: Dec. 16, 2013

(86) PCT No.: PCT/JP2013/083580
§ 371 (c)(1),
(2) Date: Jun. 15, 2015

(87) PCT Pub. No.: WO2014/098012
PCT Pub. Date: Jun. 26, 2014

(65) Prior Publication Data
US 2015/0328278 A1 Nov. 19, 2015

(30) Foreign Application Priority Data
Dec. 17, 2012 (JP) ................................ 2012-274494

(51) Int. Cl.
*A61K 38/10* (2006.01)
*A61K 35/15* (2015.01)
*C07K 14/74* (2006.01)
*C12N 5/0783* (2010.01)
*A61K 35/17* (2015.01)
*A61K 39/00* (2006.01)

(52) U.S. Cl.
CPC .............. *A61K 38/10* (2013.01); *A61K 35/15* (2013.01); *A61K 35/17* (2013.01); *A61K 39/0011* (2013.01); *C07K 14/70539* (2013.01); *C12N 5/0636* (2013.01); *A61K 2039/5154* (2013.01)

(58) Field of Classification Search
None
See application file for complete search history.

(56) References Cited

U.S. PATENT DOCUMENTS

| | | | |
|---|---|---|---|
| 7,030,212 B1 | 4/2006 | Sugiyama et al. |
| 7,063,854 B1 | 6/2006 | Gaiger et al. |
| 7,342,092 B2 | 3/2008 | Sugiyama |
| 7,378,384 B2 | 5/2008 | Sugiyama et al. |
| 7,390,871 B2 | 6/2008 | Sugiyama et al. |
| 7,420,034 B2 | 9/2008 | Sugiyama et al. |
| 7,517,950 B2 | 4/2009 | Sugiyama et al. |
| 7,608,685 B1 | 10/2009 | Sugiyama et al. |
| 7,622,119 B2 | 11/2009 | Sugiyama |
| 7,666,985 B2 | 2/2010 | Sugiyama et al. |
| 7,939,627 B2 | 5/2011 | Nishihara et al. |
| 8,105,604 B2 | 1/2012 | Sugiyama |
| 8,388,975 B2 | 3/2013 | Sugiyama |
| 8,765,687 B2 | 7/2014 | Scheinberg et al. |
| 9,233,149 B2 | 1/2016 | Scheinberg et al. |
| 2002/0128196 A1 | 9/2002 | Call et al. |
| 2004/0097703 A1 | 5/2004 | Sugiyama |
| 2004/0247609 A1 | 12/2004 | Sugiyama |
| 2005/0002951 A1 | 1/2005 | Sugiyama et al. |
| 2006/0121046 A1 | 6/2006 | Gaiger et al. |
| 2006/0165708 A1 | 7/2006 | Mayumi et al. |
| 2006/0217297 A1 | 9/2006 | Sugiyama et al. |
| 2007/0082860 A1 | 4/2007 | Sugiyama et al. |
| 2007/0128207 A1 | 6/2007 | Sugiyama |
| 2008/0070835 A1 | 3/2008 | Sugiyama |
| 2008/0152631 A1 | 6/2008 | Sugiyama |
| 2009/0099090 A1 | 4/2009 | Sugiyama et al. |
| 2009/0143291 A1 | 6/2009 | Sugiyama et al. |
| 2009/0263409 A1 | 10/2009 | Sugiyama |
| 2009/0281043 A1 | 11/2009 | Sugiyama et al. |
| 2010/0062013 A1 | 3/2010 | Sugiyama |
| 2010/0092522 A1* | 4/2010 | Scheinberg ........ A61K 39/0011 424/277.1 |

(Continued)

FOREIGN PATENT DOCUMENTS

| CN | 1671733 A | 9/2005 |
|---|---|---|
| CN | 1902313 A | 1/2007 |

(Continued)

OTHER PUBLICATIONS

Kobayashi et al. (Cancer Immunol. Immunother., 55: 850-860, 2006).*
Hohler et al. (Journal of Hepatology, 26:503-507, 1997).*
Haber, D. A., et al., "An Internal Deletion within an 11p13 Zinc Finger Gene Contributes to the Development of Wilms' Tumor", Cell, vol. 61, p. 1257-1269 (Jun. 29, 1990).
Call, K. M., et al., "Isolation and Characterization of a Zinc Finger Polypeptide Gene at the Human Chromosome 11 Wilms' Tumor Locus", Cell, vol. 60, p. 509-520 (Feb. 9, 1990).
Menke, A. L., et al., "The Wilms' Tumor 1 Gene: Oncogene or Tumor Suppressor Gene?", Int. Rev. Cytol., Vo. 181, p. 151-212 (1998).

(Continued)

*Primary Examiner* — Brad Duffy
*Assistant Examiner* — Nelson B Moseley, II
(74) *Attorney, Agent, or Firm* — Finnegan, Henderson, Farabow, Garrett & Dunner, LLP

(57) ABSTRACT

The present invention relates to a method for activating helper T cells, which includes the step of activating helper T cells by adding a WT1 peptide to antigen presenting cells, wherein the WT1 peptide has the ability to bind to an MHC class II molecule selected from HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

9 Claims, 6 Drawing Sheets

(56) References Cited

U.S. PATENT DOCUMENTS

| | | |
|---|---|---|
| 2010/0190163 A1 | 7/2010 | Sugiyama |
| 2010/0247556 A1 | 9/2010 | Sugiyama |
| 2010/0292160 A1 | 11/2010 | Sugiyama |
| 2011/0098233 A1 | 4/2011 | Sugiyama |
| 2012/0045465 A1 | 2/2012 | Sugiyama |
| 2012/0195918 A1 | 8/2012 | Sugiyama |
| 2013/0196427 A1 | 8/2013 | Sugiyama |
| 2013/0243800 A1 | 9/2013 | Sugiyama |
| 2013/0266958 A1 | 10/2013 | Sugiyama et al. |
| 2015/0328278 A1 | 11/2015 | Kubo et al. |

FOREIGN PATENT DOCUMENTS

| | | |
|---|---|---|
| EP | 1 696 027 A1 | 8/2006 |
| EP | 2 098 595 A1 | 9/2009 |
| JP | 2002-525099 A | 8/2002 |
| JP | 2006-280324 A | 10/2006 |
| WO | WO 00/18795 A2 | 4/2000 |
| WO | WO 01/62920 A2 | 8/2001 |
| WO | WO 02/099084 A2 | 12/2002 |
| WO | WO 03/002142 A1 | 1/2003 |
| WO | WO 03/028758 A1 | 4/2003 |
| WO | WO 03/106682 A1 | 12/2003 |
| WO | WO 2005/045027 A1 | 5/2005 |
| WO | WO 2005/095598 A1 | 10/2005 |
| WO | WO 2007/097358 A1 | 8/2007 |
| WO | WO 2008/081701 A1 | 7/2008 |
| WO | WO 2008/105462 A1 | 9/2008 |
| WO | WO 2010/123065 A1 | 10/2010 |
| WO | WO 2012/046730 A1 | 4/2012 |

OTHER PUBLICATIONS

Yamagami, T., et al., "Growth Inhibition of Human Leukemic Cells by WT1 (Wilms Tumor Gene) Antisense Oligodeoxynucleotides: Implications for the Involvement of WT1 in Leukemogenesis", Blood, vol. 87, No. 7, p. 2878-2884 (Apr. 1, 1996).
Inoue, K., et al., "Wilms' Tumor Gene (WT1) Competes With Differentiation-Inducing Signal in Hematopoietic Progenitor Cells", Blood, vol. 91, No. 8, p. 2969-2976 (Apr. 15, 1998).
Tsuboi, A., et al., "Constitutive expression of the Wilms' tumor gene WT1 inhibits the differentiation of myeloid progenitor cells but promotes their proliferation in response to granulocyte-colony stimulating factor (G-CSF)", Leukemia Research 23, p. 499-505 (1999).
Zeng, G., "MHC Class II-Restricted Tumor Antigens Recognized by CD4+ T Cells: New Strategies for Cancer Vaccine Design", Journal of Immunotherapy, vol. 24(3), p. 195-204 (2001).
International Preliminary Report on Patentability issued in International Application No. PCT/JP2011/072874, dated Dec. 20, 2011, 9 pages.
International Search Report issued in International Application No. PCT/JP2011/072874, dated Dec. 20, 2011, 3 pages.
Office Action issued in Examination Report in related Pakistan Patent Application No. 720/2011, dated Jan. 10, 2013, 2 pages.
May, R. J., et al., "Peptide Epitopes from the Wilms' Tumor 1 Oncoprotein Stimulate CD4+ and CD8+ T Cells That Recognize and Kill Human Malignant Mesothelioma Tumor Cells", Clin. Cancer Res., vol. 13, No. 15, p. 4547-4555 (Aug. 1, 2007).
Lehe, C., et al., The Wilms' Tumor Antigen is a Novel Target for Human CD4+ Regulatory T Cells: Implications for Immunotherapy, Cancer Research, vol. 68(15), p. 6350-6359 (Aug. 1, 2008).
Knights, A. J., et al., "Prediction of an HLA-DR-binding peptide derived from Wilms' Tumour 1 protein and demonstration of *in vitro* immunogenicity of WT1(124-138)-pulsed dentritic cells generated according to an optimized protocol", Cancer Immunol. Immunother, vol. 51, p. 271-281 (2002).
Müller, L., et al., "Synthetic peptides derived from the Wilms' tumor 1 protein human T lymphocytes to recognize chronic myelogenous leukemia cells", The Hemat. Journal, vol. 4, p. 57-66 (2003).

First Office Action issued by the State Intellectual Property Office, P. R. China in related Chinese Patent Application No. 201180058552.2, dated Apr. 9, 2014, 15 pages.
Office Action issued by the Australian Government IP Australia in related Australian Patent Application No. 2011313327, dated Jun. 2, 2014, 5 pages.
Office Action issued by the Taiwanese Intellectual Property Office in related Taiwanese Patent Application No. 100135857, dated Apr. 7, 2015, 16 pages.
Office Action issued by the Canadian Intellectual Property Office in related Canada Application No. 2,677,075, dated May 14, 2014 (3 pages).
Office Action issued by the State Intellectual Property Office, P.R. China, in related China Application No. 201310009095.9, dated Jul. 31, 2014, 9 pages.
Office Action issued by the European Patent Office in related European Application No. 11 830 662.0, dated Jun. 23, 2015, 3 pages.
Altomonte, M. et al. (2003) "Targeted therapy of solid malignancies via HLA class II antigens: a new biotherapeutic approach?" Oncogene, 22:6564-6569.
Biology Stack Exchange, Inc. "Do T-cells express MHC Molecules?" [online]biology.stackexchange.com/questions/5612. Retrieved Sep. 2014 (1 page).
Bodey, B. et al., (2000) "Failure of Cancer Vaccines: The Significant Limitations of this Approach to Immunotherapy" Anticancer Res., 20:2665-2676.
Celis, E. (2002) "Getting peptide vaccines to work: just a matter of quality control?" J. Clin. Invest., 110(12):1765-1768.
Dengjel, J. et al. (2006) "Unexpected Abundance of HLA Class II Presented Peptides in Primary Renal Cell Carcinomas" Clin. Cancer Res., 12:4163-4170.
Dermer, G.B. (1994) "Another Anniversary for the War on Cancer" Bio/Technology, 12:320.
Fournier, P. and V. Schirrmacher (2009) "Randomized clinical studies of anti-tumor vaccination: state of the art in 2008" Expert. Rev. Vaccines, 8(1):51-66.
Freshney, R.I., Culture of Animal Cells, A Manual of Basic Technique. New York: Alan R. Liss, Inc., 1983; p. 3-4.
Fujiki, F. et al. (2007) "Identification and Characterization of a WT1 (Wilms Tumor Gene) Protein-derived HLA-DRB1*0405-restricted 16-mer Helper Peptide That Promotes the Induction and Activation of WT1-specific Cytotoxic T Lymphocytes" J. Immunother. ,30(3):282-293.
Futami, S. et al. (Apr. 1995) "HLA-DRB1*1502 Allele, Subtype of DR15, Is Associated with Susceptibility to Ulcerative Colitis and Its Progression" Digestive Diseases and Sciences, 40(4):814-818.
Gao, P. et al. (2000) "Tumor Vaccination That Enhances Antitumor T-Cell Responses Does Not Inhibit the Growth of Established Tumors Even in Combination With Interleukin-12 Treatment: The Importance of Inducing Intratumoral T-Cell Migration" J. Immunother., 23:643-653.
Gao, F.G. et al. (Nov. 2002) "Antigen-specific CD4+ T-Cell Help Is Required to Activate a Memory CD8+ T Cell to a Fully Functional Tumor Killer Cell" Cancer Research, 62:6438-6441.
Genseq Accession No. AEA15677, First entry Date Jul. 28, 2005 (3 pages).
Hansen, P.W. et al. (1987) "Cytotoxic Human HLA Class II Restricted Purified Protein Derivative-Reactive T-Lymphocyte Clones. IV. Analysis of HLA Restriction Pattern and Mycobacterial Antigen Specificity" Scan. J. Immunol., 25:295-303.
Hural, J.A. et al. (2000) "Identification of Naturally Processed CD4 T Cell Epitopes from the Prostate-Specific Antigen Kallikrein 4 Using Peptide-Based in Vitro Stimulation" J. Immunol., 169(1):557-565.
Katsuhara, A. et al. (2015) "Transduction of a Novel HLA-DRB1*04:05-restricted, WT1-specific TCR Gene into Human CD4+ T Cells Confers Killing Activity Against Human Leukemia Cells" Anticancer Research, 35:1251-1262.
Klebanoff, C.A. et al. (2011) "Therapeutic cancer vaccines: are we there yet?" Immunol. Rev., 239:27-44.
Lin, Y. et al. (2013) "HLA-DPB1*05:01-restricted $WT1_{332}$-specific TCR-transduced CD4+ T Lymphocytes Display a Helper Activity

(56) References Cited

OTHER PUBLICATIONS for WT1-specific CTL Induction and a Cytotoxicity Against Leukemia Cells" *J. Immunother.*, 36(3):159-170.

Marchand, M. et al. (1999) "Tumor regressions observed in patients with metastatic melanoma treated with an antigenic peptide encoded by gene *MAGE-3* and presented by HLA-A1" *Int. J. Cancer*, 80:219-230.

Marchand, M. et al. (2001) "Biological and clinical developments inn melanoma vaccines" *Exp. Opin. Biol. Ther.*, 1(3):497-510.

Marsh, S.E. et al., *The HLA Facts Book*. London, England: Academic Press, 2000; pp. 299 and 377 (4 pages, including cover and copyright pages).

Master, P.S. et al. (1991) "Patterns of Membrane Antigen Expression by AML Blasts: Quantitation and Histogram Analysis" *Leukemia and Lymphoma*, 5:317-325.

Mustafa, A.S. and T. Godal (1987) "BCG induced CD4+ cytotoxic T cells from BCG vaccinated healthy subjects: relation between cytotoxicity and suppression *in vitro*" *Clin. Exp. Immunol.*, 69:255-262.

Rezvani, K. et al. (2005) "T-Cell Responses Directed against Multiple HLA-A*0201-Restricted Epitopes Derived from Wilms' Tumor 1 Protein in Patients with Leukemia and Healthy Donors: Identification, Quantification, and Characterization" *Clin. Cancer Res.*, 11:8799-8807.

Schreiber, T.H. et al. (2010) "Tumor immunogenicity and responsiveness to cancer vaccine therapy: The state of the art" *Seminar. Immunol.*, 22:105-112.

Sogo, Shinji, Study Director, Otsuka Pharmaceutical Co. Ltd. "Final Study Report: Effect of OVT-101 on the Helper-activity Against WT1-specific CTL From Human Peripheral Blood Mononuclear Cells" Study No. 030697, Report No. 025539; completed on Dec. 9, 2010 (22 pages).

Sogo, Shinji, Study Director, Otsuka Pharmaceutical Co. Ltd. "Final Study Report: Cytolytic Activity of OCV-501-Specific Th1 Clones" Study No. 035171, Report No. 028745; completed on Mar. 15, 2013 (39 pages).

Sotiriadou, R. et al. (2001) "Peptide HER2(776-788) represents a naturally processed broad MHC class II-restricted T cell epitope" *Br. J. Cancer*, 85(10):1527-1534.

Yazawa, T. et al. (1999) "Lack of class II transactivator causes severe deficiency of HLA-DR expression in small cell lung cancer" *J. Pathol.*, 187:191-199.

Austrailian Patent Application No. 2008220031, by International Institute of Cancer Immunology, Inc.: Patent Examination Report No. 1, dated Oct. 2, 2012 (3 pages).

Chinese Patent Application No. 200880006096.5, by International Institute of Cancer Immunology, Inc.: Office Action, dated May 5, 2011, with partial English translation.

Chinese Patent Application No. 200880006096.5, by International Institute of Cancer Immunology, Inc.: Second Office Action, dated Nov. 8, 2011, with English translation.

Chinese Patent Application No. 200880006096.5, by International Institute of Cancer Immunology, Inc.: Third Office Action, dated Mar. 28, 2012, with English translation.

Chinese Patent Application No. 200880006096.5, by International Institute of Cancer Immunology, Inc.: Reexamination Decision, dated Feb. 17, 2015, with English translation.

Chinese Patent Application No. 201310009095.9, by International Institute of Cancer Immunology, Inc.: English Translation of First Office Action and Search Report, dated Nov. 29, 2013.

Chinese Patent Application No. 201310058504.4, by International Institute of Cancer Immunology, Inc.: First Office Action and Search Report, dated Jun. 26, 2014, with English translation.

Chinese Patent Application No. 201310058504.4, by International Institute of Cancer Immunology, Inc.: Third Office Action, dated Sep. 7, 2015, with English translation.

Colombian Patent Application No. 09103858: Correspondence dated Aug. 22, 2012, from Cavelier to Aoyama & Partners, forwarding and describing Official Action (5 pages) (English).

Colombian Patent Application No. 09103858. Office Action dated May 28, 2013, with English translation (10 pages).

European Patent Application No. 08712039.0, by International Institute of Cancer Immunology, Inc.: Extended European Search Report, including Supplementary European Search Report and Search Opinion, dated Jul. 20, 2010 (6 pages).

European Patent Application No. 08712039.0, by International Institute of Cancer Immunology, Inc.: Communication pursuant to Article 94(3) EPC, dated Feb. 24, 2012 (5 pages).

European Patent Application No. 08712039.0, by International Institute of Cancer Immunology, Inc.: Summons to attend oral proceedings pursuant to Rule 115(1) EPC, dated Oct. 23, 2014 (6 pages).

Indian Patent Application No. 4956/CHENP/2009: First Examination Report, dated Dec. 12, 2013 (2 pages) (English).

International Patent Application No. PCT/JP2013/083580, filed Dec. 16, 2013, by Otsuka Pharmaceutical Co., Ltd. et al.: International Preliminary Report on Patentability, including Notification of Transmittal, dated Jul. 2, 2015 (9 pages).

International Patent Application No. PCT/JP2011/072874, filed Oct. 4, 2011, by International Institute of Cancer Immunology, Inc. et al.: International Preliminary Report on Patentability, including Notification of Transmittal, dated May 16, 2013 (10 pages).

Israel Patent Application No. 200,161, by International Institute of Cancer Immunology, Inc.: Office Action, dated Aug. 21, 2011, with English summary letter from Dr. Yitzhak Hess & Partners to Aoyama & Partners, dated Sep. 4, 2011.

Japanese Patent Application No. 2009-501276: Office Action, dated Sep. 25, 2012, with partial English translation.

Malaysian Patent Application No. PI20093253, by International Institute of Cancer Immunology, Inc.: Substantive Examination Adverse Report, including Search Report, dated Dec. 31, 2012 (3 pages) (English).

Mexican Patent Application No. MX/a/2009/009168, by International Institute of Cancer Immunology, Inc.: Correspondence dated Feb. 24, 2012, from Becerril, Coca & Becerril, S.C. to Aoyama & Partners providing an English summary of an official letter received from the Mexican Institute of Industrial Property (9 pages).

Mexican Patent Application No. MX/a/2009/009168, by International Institute of Cancer Immunology, Inc.: Correspondence dated Jun. 21, 2012, from Becerril, Coca & Becerril, S.C. to Aoyama & Partners providing an English summary of a second official letter received from the Mexican Institute of Industrial Property (5 pages).

New Zealand Application No. 5787215, by International Institute of Cancer Immunology, Inc.: Examination Report, dated Sep. 23, 2011 (2 pages).

New Zealand Application No. 5787215, by International Institute of Cancer Immunology, Inc.: Examination Report, dated Jan. 9, 2012 (3 pages).

Russian Patent Application No. 2009135802, by International Institute of Cancer Immunology: Office Action dated Dec. 12, 2011, including English translation (15 pages).

Russian Patent Application No. 2009135802, by International Institute of Cancer Immunology: Notification About Results of a Check of Patentability, dated Dec. 12, 2012, with English translation (9 pages).

Russian Patent Application No. 2009135802, by International Institute of Cancer Immunology: Official Action, dated Jun. 15, 2012, including the English translation (9 pages).

Russian Patent Application No. 2009135802, by International Institute of Cancer Immunology: Decision on Rejection to Grant a Patent for Invention, dated Aug. 14, 2013, with English translation (13 pages).

Ukrainian Patent Application No. 200909812, by International Institute of Cancer Immunology, Inc.: Official Action, dated Nov. 29, 2011, with English translation (6 pages).

Ukrainian Patent Application No. 200909812, by International Institute of Cancer Immunology, Inc.: Official Action, dated Mar. 2, 2012, with English translation (8 pages).

Vietnamese Patent Application No. 1-2009-01834, by International Institute of Cancer Immunology, Inc.: Office Action, dated May 28, 2013, with English translation (2 pages).

(56) References Cited

OTHER PUBLICATIONS

U.S. Appl. No. 12/449,765, filed Aug. 26, 2009, by Sugiyama: Non-Final Rejection, dated Apr. 3, 2012 (15 pages).
U.S. Appl. No. 12/449,765, filed Aug. 26, 2009, by Sugiyama: Final Rejection, dated Sep. 26, 2012 (11 pages).
U.S. Appl. No. 12/449,765, filed Aug. 26, 2009, by Sugiyama: Non-Final Rejection, dated Sep. 8, 2014 (14 pages).
U.S. Appl. No. 12/449,765, filed Aug. 26, 2009, by Sugiyama: Final Rejection, dated Mar. 17, 2015 (11 pages).
Knutson, K.L. and M.L. Disis (2005) "Tumor antigen-specific T helper cells in cancer immunity and immunotherapy" Cancer Immunol. Immunother., 54:721-728.
Bruening, W. et al. (May 1992) "Germline intronic and exonic mutations in the Wilms' tumour gene (*WT1*) affecting urogenital development" *Nature Genetics*, 1:144-148.
Canadian Patent Application No. 2,544,214, filed Nov. 4, 2004, by International Institute of Cancer Immunology, Inc.: Office Action, dated May 3, 2012 (3 pages).
Canadian Patent Application No. 2,544,214, filed Nov. 4, 2004, by International Institute of Cancer Immunology, Inc.: Office Action, dated Mar. 12, 2014 (2 pages).
Canadian Patent Application No. 2,544,214, filed Nov. 4, 2004, by International Institute of Cancer Immunology, Inc.: Office Action and Examination Search Report, dated Jan. 19, 2016 (3 pages).
Chinese Patent Application No. 201410573477.9, filed Feb. 27, 2008, by International Institute of Cancer Immunology, Inc.: Office Action and Search Report, dated May 31, 2016, with English translation (18 pages).
Database GenBank Accession No. AAC60604.1 (Jul. 23, 1993) "Wilms' tumor suppressor, partial [*Homo sapiens*]" [online]. National Center for Biotechnology Information (NCBI), U.S. National Library of Medicine; http://www.ncbi.nlm.nih.gov/protein/AAC60604; retrieved on Feb. 15, 2016 (1 page).
Database Geneseq Accession No. ABG52313 (Feb. 25, 2003) "Human liver peptide, SEQ ID No. 30961" [online]. Retrieved from EBI on Apr. 26, 2009, Accession No. GSN:ABG52313 (1 page).
Database Geneseq Accession No. AAG78443 (Jun. 15, 2007) "WT33 Wilm's tumour protein" [online]. Retrieved from EBI on Apr. 27, 2009, Accession No. GSP:AAG78443 (2 pages).
Database Geneseq Accession No. AAG78450 (Apr. 12, 2002) "WT33 protein fragment sequence # 1" [online]. Retrieved from EBI on Apr. 27, 2009, Accession No. GSN:AAG78450 (1 page).
Database JPO Proteins Accession No. BD589960 (Jul. 17, 2003) "Cancer vaccine comprising cationic liposome and cancer antigen based on tumor suppressor gene WT1" [online]. Retrieved from EBI on Mar. 17, 2008, Accession No. JPOP:BD589960 (1 page).
Database JPO Proteins Accession No. BD619917 (Jul. 17, 2003) "Compositions and methods for WT1 specific immunotherapy" [online]. Retrieved from EBI on Mar. 17, 2008, Accession No. JPOP:BD619917 (1 page).
European Patent Application No. 13864968.6, filed Dec. 16, 2013, by Otsuka Pharmaceutical Co., Ltd. et al.: Extended European Search Report and Search Opinion, dated Jun. 6, 2016 (7 pages).
Friede, T. et al. (1996) "Natural ligand motifs of closely related HLA-DR4 molecules predict features of rheumatoid arthritis associated peptides" *Biochim Biophys Acta*, 1316(2):85-101.
Gessler, M. et al. (Feb. 22, 1990) "Homozygous deletion in Wilms tumours of a zinc-finger gene identified by chromosome jumping" *Nature*, 343:774-778.
Healthline Networks, Inc. (2008) "Non-Hodgkin's Lymphoma: In Depth-Overview" [online]. Retrieved from the Internet: http://www.healthline.com/channel/non-hodgkins-lymnhoma_indepth-overview, on Dec. 2, 2008 (3 pages).
Indian Patent Application No. 4956/CHENP/2009: Hearing Notice, dated May 5, 2016 (2 pages).
International Patent Application No. PCT/JP2008/053417, filed Feb. 17, 2008, by International Institute of Cancer Immunology, Inc.: International Search Report, dated May 13, 2008, with English translation (5 pages).
International Patent Application No. PCT/JP2008/053417, filed Feb. 17, 2008, by International Institute of Cancer Immunology, Inc.: International Preliminary Report on Patentability, dated Sep. 1, 2009 (11 pages).
Ishioka, G.Y. et al. (1999) "Utilization of MHC class I transgenic mice for development of minigene DNA vaccines encoding multiple HLA-restricted CTL epitopes" *J Immunol*, 162(7):3915-3925.
Janeway, C.A. et al. "Chapter 3: Antigen Recognition by B-cell and T-cell Receptors" in *Immunobiology*, 5th Ed. New York: Garland Science, 2001; pp. 116-117.
Japanese Patent Application No. 2005-515303: Office Action, dated Jul. 27, 2010.
Kim, J.-H. et al. (2000) "In vitro binding analysis of hepatitis B virus preS-derived putative helper T-cell epitopes to MHC class II molecules using stable HLA-DRB1 *0405/-DRA*0101 transfected cells" *IUBMB Life*, 50:379-384.
Maffei, A. and P.E. Harris (1998) "Peptides Bound to Major Histocompatibility Complex Molecules" *Peptides*, 19(1):179-198.
Maslak, P.G. et al. (2010) "Vaccination with synthetic analog peptides derived from WT1 oncoprotein induces T-cell responses in patients with complete remission from acute myeloid leukemia" *Blood*, 116(2):171-179.
May, R.J. et al. (2006) "CD4+ peptide epitopes from the WT1 oncoprotein stimulate CD4+ and CD8+ T cells that recognize and kill leukemia and solid tumor cells" *Blood (ASH Annual Meeting Abstracts)*, 108(11 Part 1):1058A, Abstract 3706. 48th Annual Meeting of the American-Society of Hematology; Orlando, FL, USA; Dec. 9-12, 2006.
Mexican Patent Application No. MX/a/2013/003884: Office Action, dated May 25, 2016, with English translation (6 pages).
Mexican Patent Application No. MX/a/2014/002596: Office Action, dated Mar. 15, 2016, with English translation (7 pages).
Naylor, P.H. et al. (2011) "Peptide Based Vaccine Approaches for Cancer—A Novel Approach Using a WT-1 Synthetic Long Peptide and the IRX-2 Immunomodulatory Regimen" *Cancers*, 3(4):3991-4009.
Özdemir, E. et al. (Feb. 15, 1997) "HLA-DRB1*0101 and *0405 as protective alleles in Japanese patients with renal cell carcinoma" *Cancer Research*, 57(4):742-746.
Rammensee, H.G. et al. (1995) "MHC ligands and peptide motifs: first listing" *Immunogenetics*, 41(4):178-228.
Singh, H. and G.P.S. Raghava (2001) "ProPred: prediction of HLA-DR binding sites" *Bioinformatics*, 17(12):1236-1237.
Slingluff, C.L. et al. (Oct. 2001) "Phase I trial of a melanoma vaccine with gp100$_{280-288}$ peptide and tetanus helper peptide in adjuvant: immunologic and clinical outcomes" *Clinical Cancer Research*, 7(10):3012-3024.
Sugiyama, H. (2002) "Cancer Immunotherapy Targeting WT1 Protein" *Int J Hematol*, 76(2):127-132.
Tangri, S. et al. (2001) "Structural features of peptide analogs of human histocompatibility leukocyte antigen class I epitopes that are more potent and immunogenic than wild-type peptide" *J Exp Med*, 194(6):833-846.
Tsuboi, A. et al. (Dec. 2002) "Enhanced induction of human WT1-specific cytotoxic T lymphocytes with a 9-mer WT1 peptide modified at HLA-A*2402-binding residues" *Cancer Immunol Immunother*, 51(11-12):614-620.
U.S. Appl. No. 10/578,183, filed Feb. 26, 2007, by Sugiyama: Non-Final Rejection, dated Apr. 26, 2010.
U.S. Appl. No. 10/578,183, filed Feb. 26, 2007, by Sugiyama: Miscellaneous Office Action, dated Dec. 8, 2010.
U.S. Appl. No. 10/578,183, filed Feb. 26, 2007, by Sugiyama: Final Rejection, dated Oct. 12, 2011.
U.S. Appl. No. 10/578,183, filed Feb. 26, 2007, by Sugiyama: Final Rejection, dated May 24, 2012.
U.S. Appl. No. 10/578,183, filed Feb. 26, 2007, by Sugiyama: Non-Final Rejection, dated Mar. 11, 2015.
U.S. Appl. No. 10/578,183, filed Feb. 26, 2007, by Sugiyama: Final Rejection, dated Dec. 11, 2015.
U.S. Appl. No. 13/755,185, filed Jan. 31, 2013, by Sugiyama: Non-Final Rejection, dated Mar. 7, 2014.
U.S. Appl. No. 13/755,185, filed Jan. 31, 2013, by Sugiyama: Final Rejection, dated Sep. 25, 2014.

(56) References Cited

OTHER PUBLICATIONS

U.S. Appl. No. 13/755,185, filed Jan. 31, 2013, by Sugiyama: Advisory Action, dated Feb. 5, 2015.
U.S. Appl. No. 13/877,768, filed Jun. 21, 2013, by Sugiyama: Non-Final Rejection, dated Jun. 2, 2016.
Wymann, D. et al. (1999) "Human B cells secrete migration inhibition factor (MIF) and present a naturally processed MIF peptide on HLA-DRB1*0405 by a FXXL motif" *Immunology*, 96(1):1-9.
Yatsuda, J. et al. (Dec. 2013) "Establishment of HLA-DR4 Transgenic Mice for the Identification of CD4+ T Cell Epitopes of Tumor-Associated Antigens" *PLoS ONE*, 8(12):1-12.
Colombian Patent Application No. 15162173: Office Action, dated Sep. 6, 2016, with partial English Translation (16 pages).
Wang et al., "Adoptive transfer of tumor-primed, in vitro-activated, CD4+ T effector cells ($T_ES$) combined with CD8+ $T_ES$ provides intratumoral $T_E$ proliferation and synergistic antitumor response," *Blood*, 109(11); 4865-4872 (2007).
U.S. Appl. No. 12/449,765, filed Aug. 26, 2009, by Sugiyama: Final Rejection, dated Nov. 16, 2016.
International Preliminary Report on Patentability issued in corresponding International Application No. PCT/JP2013/083580, dated Feb. 25, 2014, 10 pages.
International Search Report issued in corresponding International Application No. PCT/JP2013/083580, dated Feb. 25, 2014, 5 pages.
Fujiki, F., "A Wt1 protein-derived, naturally processed 16-mer peptide, WT1$_{332}$, is a promiscuous helper peptide for induction of WT1-specific Th1-type CD4+ T cells", Microbiol. Immunol., vol. 52, p. 591-600, 10 pages (2008).
Sugiyama, H., "Wt1 Peptide-Based Cancer Immunotherapy", Biotherapy, vol. 21(5), pp. 299-306, (Sep. 2007).
Fujiki, F., "Identification of WT1 peptide which can induce WT1-specific CD4+ helper T cells in an HLA-class II-restricted manner and examination of the usefulness of the peptide", Proceedings of the Japanese Society for Immunology, 35, p. 187, 3 pages (2005).
Fujiki, F., "Identification of HLA-class II restricted WT1 peptide which can induce WT1-specific CD4+ helper T cells", Proceedings of the Japanese Society for Immunology, 34, p. 210, 3 pages (2004).
Sugiyama, H., "WT1-targeting cancer vaccine", Japanese Journal of Clinical Medicine, vol. 70, No. 12, p. 2105-2113 (2012).
Oka, Y., "Human cytotoxic T-lymphocyte responses specific for peptides of the wild-type Wilms' tumor gene (*WT1*) product", Immunogenetics, vol. 51(2) p. 99-107 (Feb. 2000).
Irie, A., et al., "Establishment of HLA-DR4 transgenic mice having antigen-presenting function to HLA-DR4-restricted CD4$^{30}$ Th cell", Japanese Society for Histocompatibility and Immunogenetics, p. 94 (Aug. 10, 2012).
Han, F., et al., "HLA-DQ association and allele competition in Chinese narcolepsy", Tissue Antigens, vol. 10(80), p. 328-335 (2012).

Megiorni, F., et al., "HLA-DQA1 and HLA-DQB1 in Celiac disease predisposition: practical implications of the HLA molecular typing". Journal of Biomedical Science, vol. 10(19:88), 5 pages (2012).
Yang. K. L., et al., "An HLA-A*02:01-B*13:01-DRB1*14:01:03 haplotype conserved in Taiwanese and a possible close relationship between DRB1*14:01:03 and DRB1*14:54", International Journal of Immunogenetics, vol. 38, p. 69-71 (2010).
House, K. D., et al., "The Search for a Missing HLA-DRB1*09 Allele", Human Immunology, vol. 10(73), p. 20, (2012).
Bardi, M. S., et al., "HLA-A, B and DRB1 allele and haplotype frequencies in volunteer bone marrow donors from the north of Parana State", Rev. Bras. Hematol. Hemoter., vol. 34(1), p. 25-30 (2012).
Gao, F. G., et al., "Antigen-specific CD4+ T-Cell Help Is Required to Activate a Memory CD8+ T Cell to a Fully Functional Tumor Killer Cell[1]", Cancer Research vol. 62(22) p. 6438-6441 (Nov. 15, 2002).
Yamagami, T., et al., "Growth Inhibition of Human Leukemic Cells by WT1 (Wilms Tumor Gene Antisense Oligodexoynucleotides: Implications for the Involvement of WT1 in Leukemogenesis", Blood, vol. 87, No. 7, p. 2878-2884 (Apr. 1, 1996).
Inoue, K., et al., "Wilms' Tumor Gene (WT1) Competes With Differentiation-Inducing Signal in Hematopoietic Progenitor Cells", Blood, vol. 91, No. 8, p. 2269-2976 (Apr. 15, 1998).
Zeng, G.J., "MHC Class II-Restricted Tumor Antigens Recognized by CD4+ T Cells: New Strategies for Cancer Vaccine Design", Journal of Immunotherapy, vol. 24(3), p. 195-204 (2001).
Lehe, C., et al., The Wilms' Tumor Antigen Is a Novel Target for Human CD4+ Regulatory T Cells: Implications for Immunotherapy, Cancer Research, vol. 68(15)p. 6350-6359 (Aug. 1, 2008).
Müller, L., et al., "Synthetic peptides derived from the Wilms' tumor 1 protein sensitize human T lymphocytes to recognize chronic nmyelogenous leukemia cells", The Hemat. Journal, vol. 4, p. 57-66 (2003).
First Office Action issued by the State Intellectual Property Office, P. R. China in related Chinese Patent Application No, 201180058552.2, dated Apr. 9, 2014, 15 pages.
Office Action issued by the State Intellectual Property Office, P.R. China, in related China Application No. 201310009095.9, dated Jul. 31 2014, 9 pages.
Non-Final Office Action dated Feb. 10, 2016 in U.S. Appl. No. 12/449,765, with Notice of References Cited (PTO-892), 20 pages.
Eurasian Patent Application No. 201591168: Office Action, dated Dec. 5, 2016, with English Translation (1 page).
U.S. Appl. No. 10/578,183, filed Feb. 27, 2007, by Sugiyama: Non-Final Rejection, dated Sep. 13, 2017 (16 pages).
U.S. Appl. No. 12/449,765, filed Aug. 26, 2009, by Sugiyama: Non-Final Rejection, dated Sep. 7, 2017 (8 pages).
U.S. Appl. No. 13/755,185, filed Jan. 31, 2013, by Sugiyama: Non-Final Rejection, dated Sep. 14, 2017 (6 pages).

* cited by examiner

SEQUENCE LISTING

```
<160> NUMBER OF SEQ ID NOS: 2

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160
```

```
Gly His Thr Pro Ser His His Ala Ala Gln Phe Pro Asn His Ser Phe
            165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
            245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
            325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
            405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu

<210> SEQ ID NO 2
<211> LENGTH: 16
<212> TYPE: PRT
<213> ORGANISM: Artificial
<220> FEATURE:
<223> OTHER INFORMATION: Synthetic peptide

<400> SEQUENCE: 2

Lys Arg Tyr Phe Lys Leu Ser His Leu Gln Met His Ser Arg Lys His
1               5                   10                  15
```

METHOD FOR ACTIVATING HELPER T CELL

TECHNICAL FIELD

The present invention relates to a method for activating helper T cells, which includes the step of activating helper T cells by adding a WT1 peptide to antigen presenting cells, wherein the WT1 peptide has the ability to bind to an MHC class II molecule selected from HLA-DRB1*08:02 molecule, HLA-DRB1*13:02 molecule, HLA-DRB1*14:03 molecule, HLA-DRB1*14:05 molecule, HLA-DQB1*03:02 molecule, and HLA-DQB1*04:01 molecule, a composition therefor, a method for activating cytotoxic T cells, an activation inducer of cytotoxic T cells (CTL), a pharmaceutical composition for treating and/or preventing a cancer by activating helper T cells and/or cytotoxic T cells, and the like. This application claims priority to and the benefit of Japanese Patent Application No. 2012-274494, filed Dec. 17, 2012, the entire contents of which is incorporated herein by reference.

BACKGROUND ART

The WT1 gene (Wilms' tumor 1 gene) was identified as a causative gene of a Wilms' tumor which is a kidney cancer in childhood, and the gene encodes a transcription factor having a zinc finger structure (Non-Patent Documents 1 and 2, herein incorporated by reference). Subsequent studies showed that the above gene serves as a cancer gene in hematopoietic organ tumors or solid cancers (Non-Patent Documents 3 to 6, herein incorporated by reference).

It was shown that cytotoxic T cells (CTLs) specific to the peptide are induced by stimulating peripheral blood mononuclear cells in vitro using a peptide having a portion of an amino acid sequence encoding the WT1 protein, and these CTLs injure cancer cells of hematopoietic organ tumors or solid cancers expressing the WT1 endogenously. The CTLs recognize the above peptide in the form of a complex bound to an MHC class I molecule, and thus the peptide differs depending on subtypes of the MHC class I (Patent Documents 1 to 4, and Non-Patent Document 7, herein incorporated by reference).

On the other hand, the presence of helper T cells specific to a cancer antigen is important in order to induce the CTLs effectively (Non-Patent Document 8, herein incorporated by reference). The helper T cells are induced and activated by recognizing a complex of an MHC class II molecule with an antigen peptide on antigen presenting cells. Activated helper T cells aid proliferation, differentiation and maturation of B cells by producing cytokines such as IL-2, IL-4, IL-5, IL-6, or interferons. Since such helper T cells have a function to activate an immune system by promoting proliferation and activation of B cells and T cells, it is suggested that the enhancement of a function of helper T cells through an MHC class II-binding antigen peptide in cancer immunotherapy to enhance effects of a cancer vaccine is useful (Non-Patent Document 9, herein incorporated by reference).

It has recently been shown that a promiscuous helper peptide which can bind to multiple MHC class II molecules and activate helper T cells is present among particular peptides having a portion of an amino acid sequence encoding a WT1 protein (hereinafter, also referred to as WT1 peptides in the present specification) (patent documents 5 and 6, herein incorporated by reference). However, it was very difficult to verify whether or not the WT1 peptides also have effects on other MHC class II molecules, because of many kinds of MHC class II molecules.

PRIOR ART DOCUMENTS

Patent Documents

Patent Document 1: International Publication No. WO 2003/106682
Patent Document 2: International Publication No. WO 2005/095598
Patent Document 3: International Publication No. WO 2007/097358
Patent Document 4: International Application No. PCT/JP2007/074146
Patent Document 5: International Publication No. WO 2005/045027
Patent Document 6: International Publication No. WO 2008/105462

Non-Patent Documents

Non-Patent Document 1: Daniel A. Haber et al., Cell. 1990 Jun. 29; 61(7):1257-69
Non-Patent Document 2: Call K M et al., Cell. 1990 Feb. 9; 60(3):509-20
Non-Patent Document 3: Menke A L. et al., Int Rev Cytol. 1998; 181:151-212. Review
Non-Patent Document 4: Yamagami T et al., Blood. 1996 Apr. 1; 87(7):2878-84
Non-Patent Document 5: Inoue K et al., Blood. 1998 Apr. 15; 91(8):2969-76
Non-Patent Document 6: Tsuboi A et al., Leuk Res. 1999 May; 23(5):499-505
Non-Patent Document 7: Oka Y et al., Immunogenetics. 2000 February; 51(2):99-107
Non-Patent Document 8: Gao F G et al., Cancer Res. 2002 Nov. 15; 62(22):6438-41
Non-Patent Document 9: Zeng G, J Immunother. 2001 May; 24(3):195-204

DISCLOSURE OF THE INVENTION

Problems to be Solved by the Invention

Accordingly, an object to be achieved by the present invention is to provide a method for activating helper T cells, a method for activating cytotoxic T cells, by applying a particular WT1 peptide to a wide range of MHC class II molecule-positive subjects, an activation inducer of cytotoxic T cells, a pharmaceutical composition for treating/preventing a cancer, and the like.

Means for Solving the Problems

Under these circumstances, the present inventors have intensively studied and found that a peptide having the amino acid sequence: Lys Arg Tyr Phe Lys Leu Ser His Leu Gln Met His Ser Arg Lys His binds to an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, and activates helper T cells and/or cytotoxic T cells. Thus, the present invention has been completed.

The present invention provides:
(1) A method for activating helper T cells, which includes the step of activating helper T cells by adding a WT1 peptide to antigen presenting cells, wherein the WT1 peptide has the ability to bind to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule;

(2) The method according to (1), wherein the WT1 peptide has the ability to bind to at least two MHC class II molecules of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule;

(3) The method according to (1) or (2), wherein the WT1 peptide further has the ability to bind to an MHC class II molecule selected from an HLA-DRB1*01:01 molecule, HLA-DRB1*04:01 molecule, HLA-DRB1*04:03 molecule, HLA-DRB1*04:05 molecule, HLA-DRB1*04:06 molecule, HLA-DRB1*08:03 molecule, HLA-DRB1*09:01 molecule, HLA-DRB1*11:01 molecule, HLA-DRB1*15:01 molecule, HLA-DRB1*15:02 molecule, HLA-DRB3*02:02 molecule, HLA-DRB4*01:01 molecule, HLA-DPB1*02:01 molecule, HLA-DPB1*03:01 molecule, HLA-DPB1*05:01 molecule, and HLA-DPB1*09:01 molecule;

(4) The method according to any one of (1) to (3), wherein the addition of a WT1 peptide to antigen presenting cells is carried out by adding a WT1 peptide, a polynucleotide encoding the WT1 peptide, an expression vector containing the polynucleotide, or cells containing the expression vector;

(5) The method according to any one of (1) to (4), wherein the WT1 peptide is a peptide containing the amino acid sequence: Lys Arg Tyr Phe Lys Leu Ser His Leu Gin Met His Ser Arg Lys His (SEQ ID NO:2), a variant or a modification thereof;

(6) A composition containing a WT1 peptide for activating helper T cells by adding the WT1 peptide to antigen presenting cells, wherein the WT1 peptide has the ability to bind to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule;

(7) The composition according to (6), wherein the WT1 peptide has the ability to bind to at least two MHC class II molecules of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule;

(8) The composition according to (6) or (7), wherein the WT1 peptide further has the ability to bind to an MHC class II molecule selected from an HLA-DRB1*01:01 molecule, HLA-DRB1*04:01 molecule, HLA-DRB1*04:03 molecule, HLA-DRB1*04:05 molecule, HLA-DRB1*04:06 molecule, HLA-DRB1*08:03 molecule, HLA-DRB1*09:01 molecule, HLA-DRB1*11:01 molecule, HLA-DRB1*15:01 molecule, HLA-DRB1*15:02 molecule, HLA-DRB3*02:02 molecule, HLA-DRB4*01:01 molecule, HLA-DPB1*02:01 molecule, HLA-DPB1*03:01 molecule, HLA-DPB1*05:01 molecule, and HLA-DPB1*09:01 molecule;

(9) The composition according to any one of (6) to (8), wherein the addition of a WT1 peptide to antigen presenting cells is carried out by adding a WT1 peptide, a polynucleotide encoding the WT1 peptide, an expression vector containing the polynucleotide, or cells containing the expression vector;

(10) The composition according to any one of (6) to (9), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof;

(11) Antigen presenting cells which present a complex of an antigen peptide containing a WT1 peptide with an MHC class II molecule, wherein the MHC class II molecule is an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule;

(12) Helper T cells which recognize a complex of an antigen peptide containing a WT1 peptide with an MHC class II molecule, wherein the MHC class II molecule is an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule;

(13) Cytotoxic T cells which are activated by the helper T cells according to (11);

(14) A pharmaceutical composition for treating or preventing a cancer, including, as an active ingredient, any of the composition according to any one of (6) to (10), the antigen presenting cells according to (11), the helper T cells according to (12), or the cytotoxic T cells according to (13);

(15) A pharmaceutical composition for activating cytotoxic T cells, including, as an active ingredient, any of a WT1 peptide, a polynucleotide encoding the WT1 peptide, an expression vector containing the polynucleotide, or cells containing the expression vector, and which is administered to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule;

(16) An antibody specifically binding to a WT1 peptide, wherein the WT1 peptide has the ability to bind to an MHC class II molecule selected from an HLA-DRB1*08:02 molecule, an HLA-DRB1*03:02 molecule, an HLA-DRB1*14:03 molecule, an HLA-DRB1*14:05 molecule, an HLA-DQB1*03:02 molecule, and an HLA-DQB1*04:01 molecule;

(17) A method for determining the presence or amount of WT1-specific helper T cells in a subject positive in respect to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, the method includes the steps of:

(a) stimulating a sample obtained from the subject using a WT1 peptide, and (b) determining the presence or amount of cytokines or helper T cells, wherein the increase of the presence or amount of cytokines or helper T cells shows the presence or amount of the WT1-specific helper T cells.

Effects of the Invention

According to the present invention, a method for activating helper T cells, a composition therefor, a method for activating cytotoxic T cells, a composition therefor, an activation inducer of cytotoxic T cells, a pharmaceutical composition for treating and/or preventing a cancer by activating helper T cells and cytotoxic T cells, and the like are obtained by applying a WT1 peptide to a subject having an MHC class II molecule selected from an HLA-DRB1*08:

02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, thus enabling activation of helper T cells and cytotoxic T cells in vivo and in vitro in subjects having such an MHC class II molecule, and treatment and prevention of a cancer, and the like.

MODES FOR CARRYING OUT THE INVENTION

Figure 1:
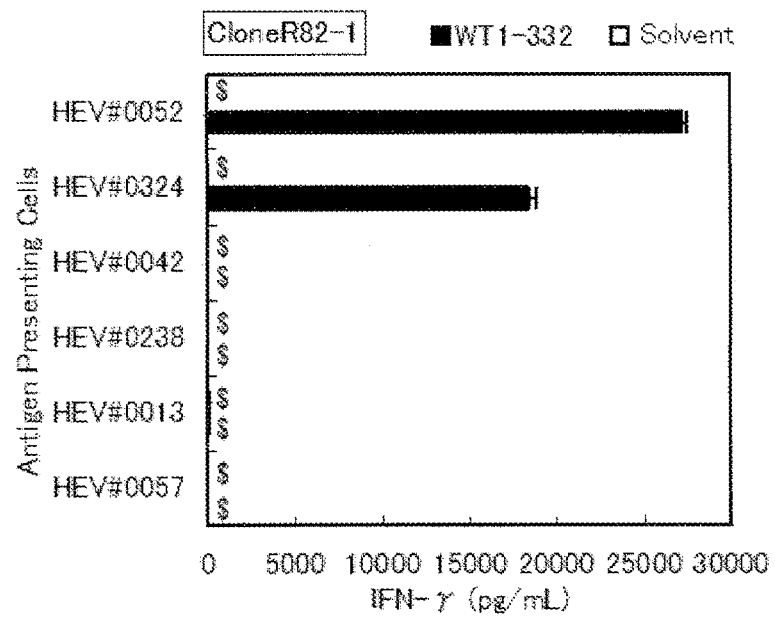
FIG. 1 shows HLA restriction of Clone R82-1. The horizontal axis shows the amount of IFN-γ production (pg/ml) upon addition of WT1-332 (black column) or solvent (white column). The vertical axis shows types of antigen presenting B-LCL cells. Data represent mean±SD (triplicates). $: Data include extrapolated value(s).

In one aspect, the present invention provides a method for activating helper T cells or cytotoxic T cells, which includes the step of activating helper T cells or cytotoxic T cells by adding a WT1 peptide to antigen presenting cells, wherein the WT1 peptide has the ability to bind to an MHC class II molecule. In the present invention, the step of activating cytotoxic T cells may be carried out by passing through the step of activating helper T cells. Also, the WT1 peptide used in the present invention is one having the ability to bind to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule. Moreover, the WT1 peptide used in the present invention may be one having the ability to bind to at least two or more MHC class II molecules of the above MHC class II molecules. Also, the WT1 peptide used in the present invention may have the ability to bind to any MHC class II molecule, for example, of HLA-DR, HLA-DQ and HLA-DP molecules.

In the present invention, the WT1 peptide may be a peptide having a portion of an amino acid sequence of a human WT1 protein depicted in SEQ ID NO:1. The peptide according to the present invention has no particular limitation in its amino acid sequence and length so far as the peptide has the above feature. However, a too long peptide is susceptible to a protease action, and a too short peptide can not bind to a peptide accommodating groove well. The length of the peptide according to the present invention is one of preferably 10 to 25 amino acids, more preferably 15 to 21 amino acids, further preferably 16 to 20 amino acids, for example, of 16 amino acids, 17 amino acids, 18 amino acids, or 19 amino acids. Specific examples of the peptide according to the present invention are those containing the amino acid sequence: Lys Arg Tyr Phe Lys Leu Ser His Leu Gln Met His Ser Arg Lys His (SEQ ID NO:2).

In addition, the WT1 peptide used in the present invention includes variants of the above peptide. The variants may contain, for example, a peptide selected from the group consisting of peptides having an amino acid sequence in which several amino acids, for example, 1 to 9, preferably 1 to 5, 1 to 4, 1 to 3, more preferably 1 to 2 amino acids, further preferably one amino acid in the amino acid sequence depicted in SEQ ID NO:2 is/are substituted, deleted or added. Substitution of amino acids in peptides may be carried out at any positions and with any types of amino acids, and conservative amino acid substitution is preferred. Examples of the conservative amino acid substitution include substitution of a Glu residue with an Asp residue, a Phe residue with a Tyr residue, a Leu residue with an Ile residue, an Ala residue with a Ser residue, a His residue with an Arg residue and the like. Preferably, addition or deletion of amino acids may be carried out at the N-terminus and the C-terminus in peptides, but may be carried out in an interior sequence. Preferred specific examples of the peptides according to the present invention are those having SEQ ID NO:2. In this connection, any of the above peptides must have the ability to bind to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, and must activate helper T cells or cytotoxic T cells (herein, also referred to as CTL). Also, human MHC molecules are generally referred to as HLA molecules, and therefore, MHC is used as a synonym of HLA in the present specification.

Moreover, the peptides according to the present invention may be those obtained by modification of the above amino acid sequence. Amino acid residues in the above amino acid sequence can be modified by a known method. Such modification may be, for example, esterification, alkylation, halogenation, phosphorylation and the like on a functional group in a side chain of an amino acid residue. Also, it is possible to bind various substances to the N-terminus and/or C-terminus of a peptide containing the above amino acid sequence. For example, an amino acid, a peptide, an analog thereof and the like may be bound to the peptide. For example, a histidine tag may be added, or a fusion protein may be formed together with a protein such as thioredoxin. Alternatively, a detectable label may be bound to the WT1 peptide. In case these substances are bound to the peptide according to the present invention, they may be treated, for example, by an in vivo enzyme and the like, or by a process such as intracellular processing to finally generate a peptide consisting of the above amino acid sequence, which is presented on cell surface as a complex with an MHC class II molecule, thereby being able to obtain an induction effect of helper T cells and/or cytotoxic T cells. These substances may be those regulating solubility of the peptide according to the present invention, those improving stability of the peptide such as protease resistance, those allowing specific delivery of the peptide of the present invention, for example, to a given tissue or organ, or those having an enhancing action of an uptake efficiency of antigen presenting cells or other action. Also, these substances may be those increasing an ability to induce CTL, for example, helper peptides other than the peptide according to the present invention.

The WT1 peptide used in the present invention can be synthesized using a method usually used in the art or a modified method thereof. Such a synthesis method is disclosed, for example, in Peptide Synthesis, Interscience, New York, 1966; The Proteins, Vol. 2, Academic Press Inc., New York, 1976; Peptide Synthesis, Maruzen Co., Ltd., 1975; Basis and Experiments of Peptide Synthesis, Maruzen Co., Ltd., 1985; Development of Medicines (continuation), Vol. 14, Peptide Synthesis, Hirokawa Shoten Co., 1991, and the like (those references are herein incorporated by reference). Also, the peptide used in the present invention can be prepared using a genetic engineering technique on the basis of information of a nucleotide sequence encoding the peptide. Such a genetic engineering technique is well known to those skilled in the art. Such a technique can be conducted according to methods such as those described in literatures (Molecular Cloning, T. Maniatis et al., CSH Laboratory (1983); DNA Cloning, D M. Glover, IRL PRESS (1985)) (those references are herein incorporated by reference).

Also, the present invention relates to a polynucleotide sequence encoding the WT1 peptide described above. The polynucleotide sequence encoding the WT1 peptide may be a DNA sequence or an RNA sequence. In the present invention, such a polynucleotide sequence may be used instead of the WT1 peptide. Such a polynucleotide sequence may be used by integrating into a suitable vector. The vector includes plasmids, phage vectors, virus vectors and the like, for example, pUC118, pUC119, pBR322, pCR3, pYES2, pYEUra3, pKCR, pCDM8, pGL2, pcDNA3.1, pRc/RSV, pRc/CMV, pAcSGHisNT-A, λZAPII, λgt11 and the like. The vector may contain, as needed, factors such as an expression-inducible promoter, a gene encoding a signal sequence, a marker gene for selection, and a terminator. A method for introducing these genes into cells or living bodies, a method for expressing them and the like are known to those skilled in the art.

The antigen presenting cells used in the present invention are those which can present an antigen peptide containing the above WT1 peptide together with an MHC class II molecule to helper T cells, and mean, for example, dendritic cells, peripheral blood mononuclear cells and the like. Accordingly, subjects from which the antigen presenting cells used in the present invention are derived must have the same molecule as an MHC class II molecule to which the WT1 peptide added can bind (for example, any one or more MHC class II molecules of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule).

In the present invention, addition of the WT1 peptide to antigen presenting cells may be carried out directly by addition of the WT1 peptide, or indirectly by addition of a polynucleotide encoding the WT1 peptide or of an expression vector containing a polynucleotide encoding the WT1 peptide or by addition of cells containing the expression vector. Specifically, the addition of a WT1 peptide to antigen presenting cells may be carried out by having the antigen presenting cells contact with the WT1 peptide, or introducing a polynucleotide encoding the WT1 peptide or an expression vector containing the polynucleotide into the antigen presenting cells. The above addition can be carried out by a method known in the art. The above polynucleotide encoding the WT1 peptide, expression vector containing a polynucleotide encoding the WT1 peptide, and cells containing the expression vector can be obtained by a technique well known to those skilled in the art. Specifically, the polynucleotide used in the present invention can be determined on the basis of an amino acid sequence of the above WT1 peptide (for example, the amino acid sequence depicted in SEQ ID NO:2). The above polynucleotide can be prepared, for example, by a DNA or RNA synthesis, a PCR method and the like. Also, the types of expression vectors containing the above polynucleotide, sequences contained in addition to the above polynucleotide sequence and the like can be selected properly depending on the purposes, types and the like of hosts into which the expression vectors are introduced. The expression vectors include plasmids, phage vectors, virus vectors and the like. The cells containing an expression vector can be prepared, for example, by transforming host cells. The host cells include *Escherichia coli* cells, yeast cells, insect cells, animal cells and the like. A method for transforming host cells may be a conventional method, and it is possible to use, for example, a calcium phosphate method, a DEAE-dextran method, an electroporation method, and a lipid for gene transfer.

In general, helper T cells are activated when a TCR-CD3 complex on a T cell surface recognizes an antigen peptide through an MHC class II molecule on a surface of antigen presenting cells, and integrin on a T cell surface is stimulated by an integrin ligand on a surface of antigen presenting cells. The activation of helper T cells in the present specification includes not only the activation of helper T cells but also induction and proliferation of helper T cells. Also, helper T cells activated in the present invention may be undifferentiated T cells (for example, naive T cells) and the like. The activated helper T cells have a function that activates an immune system by promoting induction, proliferation and activation of B cells and cytotoxic T cells. Accordingly, the method of the present invention can be used as an adjunctive therapy for treating a cancer and the like. Also, helper T cells activated in vitro using the method of the present invention can be used for treating or preventing a cancer and the like, or as an adjunctive agent therefor. The activation of helper T cells can be evaluated, for example, by measuring the production or secretion of cytokines such as interferons (for example, interferon-γ, etc.) and interleukins.

In another aspect, the present invention provides a composition for activating helper T cells or cytotoxic T cells by adding a WT1 peptide to antigen presenting cells. In the present invention, the activation of cytotoxic T cells may be carried out by passing through the activation of helper T cells. Although a WT1 peptide, a polynucleotide encoding the WT1 peptide, a vector containing the polynucleotide, and cells containing the vector can be exemplified in the composition of the present invention, any molecules may be used providing that they are factors capable of presenting a WT1 peptide as an antigen peptide on a surface of antigen presenting cells. These factors can be obtained by a method well known to those skilled in the art as described above.

The WT1 peptide used in the present invention has the ability to bind to any of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, as described above. Also, the WT1 peptide used in the present invention may have the ability to bind to at least two or more MHC class II molecules of the above MHC class II molecules. Moreover, the WT1 peptide used in the present invention may have the ability to bind to any MHC class II molecule of HLA-DR, HLA-DQ, or HLA-DP molecules.

When the composition of the present invention is administered to a subject having any one or more MHC class II molecules of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, an immune system is activated by activation of helper T cells and/or cytotoxic T cells in the subject. Also, the WT1 gene is highly expressed in various cancers and tumors, for example, in hematological malignancy such as leukemia, myelodysplastic syndrome, multiple myeloma and malignant lymphoma, as well as in solid cancers such as stomach cancer, colorectal cancer, lung cancer, breast cancer, germ-cell cancer, liver cancer, skin cancer, bladder cancer, prostate cancer, uterus cancer, cervical cancer and ovary cancer, and therefore, the composition of the present invention can be used as an adjunctive agent for treating or preventing a cancer. Alternatively, helper T cells, cytotoxic T cells and the like, which are activated using the composition of the present invention, can be used, for example, as an adjunctive agent for treating the above cancers.

In addition to the above WT1 peptide, polynucleotide encoding the WT1 peptide, vector containing the polynucleotide, and cells containing the vector, the composition of the present invention may contain, for example, a carrier, an excipient, an additive and the like. The above WT1 peptide and the like contained in the composition of the present invention activate helper T cells and/or cytotoxic T cells in a WT1 peptide-specific manner, and therefore, the composition may contain a known MHC class I-restrictive WT1 peptide, or may be applied together with such a peptide.

A method for applying the composition of the present invention can be selected properly depending on conditions such as the desired degree of activation of helper T cells and/or cytotoxic T cells, and the state of antigen presenting cells. The application method includes, for example, administration to a subject by intradermal administration, subcutaneous administration, intramuscular administration, intravenous administration, transnasal administration, oral administration and the like, or addition to a culture fluid of antigen presenting cells, but is not limited thereto. The amount of the above WT1 peptide and the like contained in the composition of the present invention, the form of the composition, the application frequency of the composition and the like can be selected properly depending on conditions such as the desired degree of activation of helper T cells and/or cytotoxic T cells, and the state of antigen presenting cells.

In still another aspect, the present invention provides a method for treating or preventing a cancer in a subject, which includes the step of activating helper T cells or cytotoxic T cells by adding a WT1 peptide to antigen presenting cells, wherein the WT1 peptide has the ability to bind to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule. The method of the present invention activates an immune system in a subject by activating helper T cells and/or cytotoxic T cells, thereby treating or preventing a cancer in a subject. In the method of the present invention, the step of activating cytotoxic T cells may be carried out by passing through the step of activating helper T cells. The addition of the WT1 peptide to antigen presenting cells may be carried out directly by addition of the WT1 peptide, or indirectly by addition of a polynucleotide encoding the WT1 peptide or of an expression vector containing a polynucleotide encoding the WT1 peptide or by addition of cells containing the expression vector. The above polynucleotide encoding the WT1 peptide, expression vector containing a polynucleotide encoding the WT1 peptide, and cells containing the expression vector can be obtained by a method well known to those skilled in the art, as described above. Subjects to which the method of the present invention can be applied are those positive in respect to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule. Cancers to which the present invention can be applied may be any cancers, and include, for example, hematopoietic organ tumors such as leukemia, myelodysplastic syndrome, multiple myeloma and malignant lymphoma, as well as solid cancers such as stomach cancer, bowel cancer, lung cancer, breast cancer, germ-cell cancer, liver cancer, skin cancer, bladder cancer, prostate cancer, uterus cancer, cervical cancer and ovary cancer. Also, the method of the present invention may be used together with a method for treating or preventing a cancer using an MHC class I molecule-restrictive WT1 peptide or a pharmaceutical composition therefor.

In still another aspect, the present invention provides use of a WT1 peptide for preparing the above composition, of a polynucleotide encoding the WT1 peptide, of a vector containing the polynucleotide, and of cells containing the vector.

In still further aspect, the present invention relates to a kit containing the above WT1 peptide, polynucleotide encoding the WT1 peptide, vector containing the polynucleotide, or cells containing the vector, for activating helper T cells and/or cytotoxic T cells by adding the WT1 peptide to antigen presenting cells, wherein the WT1 peptide has the ability to bind to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule. Preferably, the kit is used in the above method for activating helper T cells or cytotoxic T cells. The kit of the present invention may contain, for example, an obtaining means of antigen presenting cells, an evaluating means of activity of helper T cells and/or cytotoxic T cells and the like, in addition to the WT1 peptide. In general, the kit is accompanied with an instruction manual. It is possible to effectively activate helper T cells or cytotoxic T cells using the kit of the present invention.

In another aspect, the present invention provides antigen presenting cells which present a complex of an antigen peptide containing a WT1 peptide with an MHC class II molecule. In this case, the MHC class II molecule may be any molecule of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, or may be at least two or more molecules of the above MHC class II molecules. The antigen presenting cells of the present invention may be prepared using a technique known to those skilled in the art. For example, they may be prepared by isolating cells having an antigen presenting ability from a cancer patient, and then pulsing the isolated cells with the above WT1 peptide (for example, peptide having the amino acid sequence as shown in SEQ ID NO:2) or with a polynucleotide encoding the WT1 peptide, or introducing an expression vector containing the polynucleotide into the cells, thereby allowing a complex of an antigen peptide containing the WT1 peptide with an MHC class II molecule to present on the cell surface (Cancer Immunol. Immunother. 46:82, 1998, J. Immunol., 158: p 1796, 1997, Cancer Res., 59: p 1184, 1999, Cancer Res., 56: p 5672, 1996, J. Immunol., 161: p 5607, 1998, J. Exp. Med., 184: p 465, 1996) (those references are herein incorporated by reference). In the present specification, the cells having an antigen presenting ability are not limited so far as they express an MHC class II molecule capable of presenting a WT1 peptide on the cell surface, and peripheral blood mononuclear cells or dendritic cells having a high antigen presenting ability are preferred. Also, the presence of the antigen presenting cells of the present invention is confirmed by an increase of activity of cytotoxic T cells, which is confirmed by an increase of an amount of interferon-γ, as shown in the Examples. The antigen presenting cells of the present invention are effectively used in a cell therapy (for example, dendritic cell therapy) as an active ingredient of a pharmaceutical composition.

In still another aspect, the present invention provides helper T cells which recognize a complex of an antigen peptide containing a WT1 peptide with an MHC class II molecule. In this case, the MHC class II molecule may be any molecule of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, or may be at least two or more molecules of the above MHC class II molecules. The helper T cells of the present invention include, for example, those recognizing a complex of an antigen peptide containing a peptide consisting of the amino acid sequence depicted in SEQ ID NO:2 with an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule. The helper T cells of the present invention can easily be prepared and obtained by those skilled in the art using a technique known in the art (Iwata, M. et al., Eur. J. Immunol, 26, 2081 (1996)) (the reference is herein incorporated by reference).

In still another aspect, the present invention provides cytotoxic T cells which are activated by helper T cells recognizing a complex of an antigen peptide containing a WT1 peptide with an MHC class II molecule. The cytotoxic T cells of the present invention include, for example, those activated by helper T cells recognizing a complex of an antigen peptide containing a peptide consisting of the amino acid sequence as shown in SEQ ID NO:2 with an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule. The cytotoxic T cells of the present invention can easily be prepared by those skilled in the art using a known technique. For example, they are prepared by isolating peripheral blood lymphocytes from a patient, and stimulating them in vitro with a peptide (for example, peptide having the amino acid sequence depicted in SEQ ID NO:2), a polynucleotide encoding the peptide, or an expression vector containing the polynucleotide (Journal of Experimental Medicine 1999, 190:1669) (the reference is herein incorporated by reference). The cytotoxic T cells thus prepared can be used as an active ingredient of a pharmaceutical composition for treating or preventing a cancer and the like.

In still another aspect, the present invention provides an HLA tetramer having the above antigen peptide containing a WT1 peptide and an MHC class II molecule. The MHC class II molecule may be any molecule of an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, or may be at least two or more molecules of the above MHC class II molecules. In the present specification, the HLA tetramer means a tetramerized product which is obtained by biotinylating a complex (HLA monomer) obtained by association of an HLA protein with a peptide, and then binding the biotinylated product to avidin. HLA tetramers containing various antigen peptides are commercially available, and it is possible to prepare the HLA tetramer of the present invention easily (Science 279: 2103-2106 (1998), Science 274: 94-96 (1996)) (the reference is herein incorporated by reference). The tetramer of the present invention is preferably labeled with fluorescence so that the bound helper T cells and cytotoxic T cells of the present invention can be selected or detected easily by a known detecting means such as flow cytometry and fluorescence microscope. The HLA tetramer in the present invention is not limited to a tetramer, and it is also possible to use a multimer such as a pentamer and a dendrimer, as needed. In the present specification, the multimer means a multimerized product which is obtained by binding two or more complexes (HLA monomers) obtained by association of an HLA protein with a peptide using a known technique.

In another aspect, the present invention provides a pharmaceutical composition for activating helper T cells or cytotoxic T cells, which contains, as an active ingredient, any of the above-mentioned composition, antigen presenting cells, helper T cells, cytotoxic T cells or tetramer. The pharmaceutical composition of the present invention may contain, as an active ingredient, any one or more of the above-mentioned composition, antigen presenting cells, helper T cells, cytotoxic T cells or tetramer. The pharmaceutical composition of the present invention can be used for treating or preventing a cancer. The pharmaceutical composition of the present invention can be applied to various cancers and tumors expressing WT1, for example, to hematopoietic organ tumors such as leukemia, myelodysplastic syndrome, multiple myeloma and malignant lymphoma, as well as to solid cancers such as stomach cancer, bowel cancer, lung cancer, breast cancer, germ-cell cancer, liver cancer, skin cancer, bladder cancer, prostate cancer, uterus cancer, cervical cancer and ovary cancer. Also, the pharmaceutical composition of the present invention can be used for administering to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule. The pharmaceutical composition of the present invention may be used together with other method for treating or preventing a cancer or pharmaceutical composition therefor. Moreover, the pharmaceutical composition of the present invention may contain an activating agent, a proliferating agent, an inducing agent and the like of helper T cells or cytotoxic T cells, or may contain a known MHC class I-restrictive WT1 peptide.

In addition to an active ingredient, the pharmaceutical composition of the present invention may contain, for example, a carrier, an excipients and the like. The administration method of the pharmaceutical composition of the present invention can be selected properly depending on conditions such as a type of diseases, a state of subjects and a target site. The method includes, for example, intradermal administration, subcutaneous administration, intramuscular administration, intravenous administration, transnasal administration, oral administration and the like, but is not limited thereto. The amount of the above active ingredient contained in the pharmaceutical composition of the present invention, the dosage form of the composition, the administration frequency of the composition and the like can be selected properly depending on conditions such as a type of diseases, a state of subjects, a target site and the like.

In still another aspect, the present invention provides a method for treating or preventing a cancer, which include the step of administering any of the above-mentioned composition, antigen presenting cells, helper T cells, cytotoxic T cells or tetramer to a subject in an effective amount, wherein the subject has an MHC class II molecule selected from an HLA-DRB1*08:02 molecule, an HLA-DRB1*13:02 molecule, an HLA-DRB1*14:03 molecule, an HLA-DRB1*14: 05 molecule, an HLA-DQB1*03:02 molecule, and an HLA-DQB1*04:01 molecule. Cancers which can be treated or prevented by the method of the present invention are various cancers and tumors expressing WT1, for example, hematopoietic organ tumors such as leukemia, myelodysplastic syndrome, multiple myeloma and malignant lymphoma, as well as solid cancers such as stomach cancer, bowel cancer, lung cancer, breast cancer, germ-cell cancer, liver cancer, skin cancer, bladder cancer, prostate cancer, uterus cancer, cervical cancer and ovary cancer. The method of the present invention may be used together with other method for treating or preventing a cancer, for example, a method for treating or preventing a cancer using a known MHC class I molecule-restrictive WT1 peptide.

In still another aspect, the present invention provides use of any of the above-mentioned composition, antigen presenting cells, helper T cells, cytotoxic T cells or tetramer for preparing the above pharmaceutical composition.

In one aspect, the present invention relates to an antibody which specifically binds to the above WT1 peptide or polynucleotide encoding the WT1 peptide (hereinafter, the antibody is also referred to as an anti-WT1 antibody). The antibody of the present invention may be either of a polyclonal antibody or a monoclonal antibody. Specifically, an antibody which specifically binds to a peptide having the amino acid sequence as shown in SEQ ID NO:2 and the like may be mentioned. A method for preparing such an antibody is already known, and the antibody of the present invention can be prepared according to such a conventional method as well (Current protocols in Molecular Biology, Ausubel et al. (ed.), 1987, John Wiley and Sons (pub.), Section 11.12-11.13, Antibodies; A Laboratory Manual, Lane, H. D. et al. (ed.), Cold Spring Harbor Laboratory Press (pub.), New York, 1989) (those references are herein incorporated by reference). For example, a nonhuman animal such as domestic rabbit is immunized using a peptide having the amino acid sequence depicted in SEQ ID NO:2 as an immunogen, and a polyclonal antibody can be obtained from a serum of the animal by a conventional method. On the other hand, in the case of a monoclonal antibody, a nonhuman animal such as mouse is immunized using the peptide used in the present invention (a peptide having the amino acid sequence depicted in SEQ ID NO:2), and the resulting spleen cells and myeloma cells are fused to prepare hybridoma cells, from which the monoclonal antibody can be obtained (Current protocols in Molecular Biology, Ausubel et al. (ed.), 1987, John Wiley and Sons (pub.), Section 11.4-11.11) (the reference is herein incorporated by reference). Also, the preparation of the anti-WT1 antibody of the present invention can be carried out by boosting an immunological reaction using various adjuvants depending on a host. Such adjuvants include a mineral gel (for example, Freund's adjuvant, aluminum hydroxide, etc.), a surfactant, a human adjuvant and the like. The anti-WT1 antibody of the present invention can be used for affinity chromatography, immunological diagnosis and the like. A method for the immunological diagnosis can be selected properly from immunoblotting, radioimmunoassay (RIA), enzyme-linked immunosorbent assay (ELISA), fluorescent or luminescent measurement and the like.

In another aspect, the present invention provides a method for determining the presence or amount of a WT1 peptide in a subject positive in respect to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, the method including the steps of:

(a) reacting a sample obtained from the subject with the above anti-WT1 antibody, and then (b) determining the presence or amount of the above anti-WT1 antibody contained in the sample.

A sample obtained from a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule can be used as a sample used in the above step (a). Samples used in the above step (a) include, for example, body fluid and tissues such as blood and lymphocytes. Those skilled in the art can properly obtain samples, react them with an antibody and carry out other procedures using a known technique. The step (b) in the present invention includes, for example, determination of the localization, site, amount and the like of the above anti-WT1 antibody, and therefore, the present invention can be used for diagnosis, prognosis and the like of a cancer. The above anti-WT1 antibody may be labeled. As a label, known labels such as a fluorescent label and a radioactive label can be used. By labeling, it becomes possible to carry out the determination of the presence or amount of a WT1 peptide simply and rapidly.

In still another aspect, the present invention relates to a kit for determining the presence or amount of a WT1 peptide, which contains the above anti-WT1 antibody as an essential constituent. The kit of the present invention may contain, for example, means for obtaining the anti-WT1 antibody and means for evaluating anti-WT1 antibody, and the like, in addition to the above anti-WT1 antibody. In general, the kit is accompanied with an instruction manual. By using the kit of the present invention, it becomes possible to determine the presence or amount of a WT1 peptide simply and rapidly in the above method for determining the presence or amount of a WT1 peptide.

In still another aspect, the present invention provides a method for determining the presence or amount of WT1- specific helper T cells or WT1-specific cytotoxic T cells in a subject positive in respect to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, the method including the steps of:

(a) stimulating a sample obtained from the subject using a WT1 peptide, and (b) determining the presence or amount of cytokines, helper T cells or cytotoxic T cells, and wherein the increase of the presence or amount of cytokines, helper T cells or cytotoxic T cells shows the presence or amount of the WT1-specific helper T cells or WT1-specific cytotoxic T cells.

Samples in the present invention may be any samples so far as they contain antigen presenting cells, and include, for example, peripheral blood mononuclear cells, invasive lymphocytes, tumor cells, cells in ascites fluid, cells in pleural effusion, cells in cerebrospinal fluid, bone marrow cells, lymph node cells and the like. The sample used in the present invention may be derived from healthy donors or from cancer patients. By using those cells derived from healthy donors, for example, it becomes possible to diagnose whether the donors are affected by a cancer, or whether the donors have a predisposition of a cancer, or other conditions. By using those cells derived from cancer patients, for example, it becomes possible to predict whether a WT1 immunotherapy has an effect in the cancer patients, or other conditions. In the method of the present invention, samples obtained may be cultured before and after stimulation with a WT1 peptide, and the culture conditions can be determined properly by those skilled in the art. The stimulation of these cells with a WT1 peptide can be carried out using a known technique such as electroporation, and may be carried out either in vitro or in vivo. The production of a cytokine, the presence of a reaction of helper T cells or cytotoxic T cells, the amount of a cytokine produced, or the amount of helper T cells or cytotoxic T cells reacted can be determined by a known method.

In still another aspect, the present invention relates to a kit for determining the presence or amount of a WT1 peptide, which contains the above WT1 peptide as an essential component. The kit of the present invention may contain, for example, an obtaining means of samples, an evaluating means such as cytokines, in addition to the above WT1 peptide. In general, the kit is attached with an instruction manual. By using the kit of the present invention, it becomes possible to determine the presence or amount of a WT1 peptide simply and rapidly in the above method for determining the presence or amount of a WT1 peptide.

The present invention also provides:

a composition comprising a WT1 peptide for activating helper T cells by adding the WT1 peptide to antigen presenting cells, wherein helper T cells recognize a complex of the WT1 peptide and an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, and a pharmaceutical composition for treating or preventing a cancer which comprises the composition as an active ingredient;

a pharmaceutical composition for treating or preventing a cancer, comprising, as an active ingredient, any of a WT1 peptide, a polynucleotide encoding the WT1 peptide, an expression vector containing the polynucleotide, or cells containing the expression vector, and which is administered to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule; and a method for activating helper T cells, which comprises the step of activating helper T cells by adding a WT1 peptide to antigen presenting cells, wherein helper T cells recognize a complex of the WT1 peptide and an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

The present invention also provides the followings:

(1) A composition for activating helper T cells which comprises a WT1 peptide, a polynucleotide encoding the WT1 peptide, an expression vector containing the polynucleotide, or cells containing the expression vector, wherein helper T cells recognize a complex of the WT1 peptide and an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(2) A composition for activating cytotoxic T cells which comprises a WT1 peptide, a polynucleotide encoding the WT1 peptide, an expression vector containing the polynucleotide, or cells containing the expression vector, wherein the composition is administered to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(3) A composition for treating or preventing a cancer which comprises a WT1 peptide, a polynucleotide encoding the WT1 peptide, an expression vector containing the polynucleotide, or cells containing the expression vector, wherein the composition is administered to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(4) The composition according to any one of (1)-(3), which comprises a WT1 peptide.

(5) The composition according to any one of (1)-(4), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof.

(6) The composition according to (5), wherein the WT1 peptide is a peptide containing the amino acid sequence: Lys Arg Tyr Phe Lys Leu Ser His Leu Gln Met His Ser Arg Lys His (SEQ ID NO:2).

(7) Antigen presenting cells which present a complex of an antigen peptide containing a WT1 peptide with an MHC class II molecule, wherein the MHC class II molecule is an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(8) The antigen presenting cells according to (7), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof.

(9) The antigen presenting cells according to (8), wherein the WT1 peptide is a peptide containing the amino acid sequence: Lys Arg Tyr Phe Lys Leu Ser His Leu Gln Met His Ser Arg Lys His (SEQ ID NO:2).

(10) Helper T cells which recognize a complex of an antigen peptide containing a WT1 peptide with an MHC class II molecule, wherein the MHC class II molecule is an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(11) The Helper T cells according to (10), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof.

(12) The Helper T cells according to (11), wherein the WT1 peptide is a peptide containing the amino acid sequence:

```
                                              (SEQ ID NO: 2)
Lys Arg Tyr Phe Lys Leu Ser His Leu Gln Met His

Ser Arg Lys His.
```

(13) Cytotoxic T cells which are activated by the helper T cells according to (12).

(14) A pharmaceutical composition for treating or preventing a cancer, comprising, as an active ingredient, any of the antigen presenting cells according to any one of (7)-(9), the helper T cells according to any one of (10)-(12), or the cytotoxic T cells according to claim (13).

The present invention also provides the followings:
(1) A method for activating helper T cells, which comprises the step of activating helper T cells by adding a WT1 peptide to antigen presenting cells, wherein helper T cells recognize a complex of the WT1 peptide and an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(2) The method according to (1), wherein the addition of a WT1 peptide to antigen presenting cells is carried out by having the antigen presenting cells contact with the WT1 peptide, or introducing a polynucleotide encoding the WT1 peptide or an expression vector containing the polynucleotide into the antigen presenting cells.

(3) A method for activating cytotoxic T cells, which comprises administering a WT1 peptide, a polynucleotide encoding the WT1 peptide, an expression vector containing the polynucleotide, or cells containing the expression vector to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(4) A method for treating or preventing a cancer, which comprises administering WT1 peptide, a polynucleotide encoding the WT1 peptide, an expression vector containing the polynucleotide, or cells containing the expression vector to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(5) The method according to any one of (1)-(4), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof.

(6) The method according to (5), wherein the WT1 peptide is a peptide containing the amino acid sequence: Lys Arg Tyr Phe Lys Leu Set His Leu Gln Met His Ser Arg Lys His (SEQ ID NO:2).

The present invention also provides the followings:
(1) Use of a WT1 peptide, a polynucleotide encoding the WT1 peptide, an expression vector containing the polynucleotide, or cells containing the expression vector for the preparation of a medicament for activating helper T cells, wherein helper T cells recognize a complex of the WT1 peptide and an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(2) Use of a WT1 peptide, a polynucleotide encoding the WT1 peptide, an expression vector containing the polynucleotide, or cells containing the expression vector for the preparation of a medicament for activating cytotoxic T cells, wherein the medicament is administered to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(3) Use of a WT1 peptide, a polynucleotide encoding the WT1 peptide, an expression vector containing the polynucleotide, or cells containing the expression vector for the preparation of a medicament to treat or prevent a cancer, wherein the medicament is administered to a subject having an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

(4) The use according to any one of (1)-(3), for the preparation of a medicament comprising a WT1 peptide.

(5) The use according to any one of (1)-(4), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof.

(6) The use according to (5), wherein the WT1 peptide is a peptide containing the amino acid sequence: Lys Arg Tyr Phe Lys Leu Ser His Leu Gln Met His Ser Arg Lys His (SEQ ID NO:2).

The present invention will be described in detail and specifically by way of examples, but they should not be construed as limiting the present invention.

EXAMPLES

Example 1: Establishment of WT1 Peptide (SEQ ID NO: 2)-Specific Th1 Clone Cells

WT1 peptide (SEQ ID NO: 2) (referred to as WT1-332 hereinafter)-specific Th1 clone cells (referred to as "the Th1 clone cells" hereinafter) was established as described below.

(1) Test Materials
Main materials used are indicated below.
Test Compound

TABLE 1

| Compound Name | Lot Number | Supplier |
|---|---|---|
| WT1-332* | 100521 | American Peptide Company, Inc. |

Storage conditions: freezer preset at −30° C.
*WT1-332: Lys Arg Tyr Phe Lys Leu Ser His Leu Gln Met His Ser Arg Lys His (SEQ ID NO: 2)

Preparation of Test Compound
WT1-332 was dissolved in 10 mM acetic acid at 20 mg/mL. The solution was sterilized by filtration and stored in a freezer preset at −30° C.
Peripheral blood mononuclear cell (PBMC) as feeder cell
1) Name of cell: PBMC
2) Source: Peripheral blood from healthy human adult donor
After linkable anonymizing was performed and written informed consent was obtained under the control of a personal information manager, blood was obtained from the donor and manipulated in this experiment.
3) Sample condition: Any of feeders is different from the sample for cloning.
4) Blood collection: 40 mL of heparinized peripheral blood
B-LCL cell line as feeder cell
5) Name of cell: B-LCL cell line
6) Source: Human peripheral blood
7) Supplier: RIKEN CELL BANK or IHWG CELL BANK Groups

TABLE 2

| Group # | Agent | Measurement | Well* |
|---|---|---|---|
| 1 | solvent | ICS or Production of IFN-γ (pg/ml) | 1 or 3 |
| 2 | WT1-332 | | |

*After the intracelllar cytokine staining (ICS) and cloning, th first test of ELISA was conducted in one well.

Reagents
Among the reagents used in the test, important ones were listed below.

TABLE 3

| Name | Cat number | Supplier |
|---|---|---|
| OptEIA ELISA set (human IFN-γ) | 555142 | BD Biosciences |
| BD OptEIA Reagent Set B | 550534 | BD Biosciences |
| Phytohaemagglutinin (PHA) | 30852801 | remel. |
| MACS CD4 MicroBeads | 120-000-440 | Milteny Biotec |

Preparation of Culture Medium
Human AB Serum and Fetal bovine serum (FBS) were used after inactivation and filtration through a 0.2 μm filter. Twenty U/mL heparin HBSS, 10% FBS/RPMI-1640 (100 units/mL penicillin, 100 μg/mL streptomycin), and 10% human AB serum-containing AIM-V (Invitrogen) were used for PBMC separation, B-LCL cell culture, and other culture, respectively. Cell culture was performed in a 37° C.-5% $CO_2$ incubator in each medium.
(2) Test Methods
Preparation of PBMC
PBMCs were prepared by density centrifugation from peripheral blood of healthy volunteers and a part of the PBMCs was used to induce WT1-332-specific T cells. The remaining cells were cryopreserved in a cell banker (Juji Field Inc.) and used as feeder cells or antigen-presenting cells for re-stimulation.
Induction of WT1-332-Specific T Cell
The PBMCs thus prepared were seeded on 24-well plates at $1.5 \times 10^6$ cells/well in 10 wells and added with WT1-332 at a final concentration of 20 μg/mL and IL-7 at a final concentration of 10 ng/mL and stared to be cultured (Day 0, total medium volume: 2 mL/well).
After 1 week, the cells were re-stimulated. First, PBMCs adjusted to $3.0 \times 10^6$ cells/well or less for antigen presentation were cultured for 2 hours with WT1-332 at a final concentration of 20 μg/mL, and further cultured for 45 min with mitomycin C (MMC) (final concentration=50 μg/mL), and then, after washed with AIM-V, the cells were used as antigen presenting cells. Next, after the cultured PBMCs were collected and adherent cells were removed, the remaining cells were seeded at $1.15-1.43 \times 10^6$ cells/well and again cultured with the same number of WT1/MMC-treated antigen presenting cells added with IL-7 at a final concentration of 10 ng/ml (Day 7). Two days later, half of the medium was changed with 40 U/mL IL-2 containing medium, and the cells were further cultured for one week while half of the medium was changed with 20 U/mL IL-2 containing medium every other day.
Intracellular Cytokine Staining (ICS)
On Day 14, the cultured cells were collected and seeded on a 96 well round-bottom plate at $2.0 \times 10^5$ cells/well in two wells, and then cultured for 4 hours added with 20 μg/mL WT1-332 in one well and with the solvent in another well and further cultured for 2 hours added with 1× Brefeldin (final concentration). The cells were collected, added with PE-labeled anti-human CD4 antibody and FITC-labeled anti-human CD8 antibody, and incubated for 15 minutes at 4° C. After washed with Staining Buffer, the cells were added with Cytofix Cytoperm Fix/Perm, and treated for 20 minutes at 4° C. Alter washed with Perm./Wash Buffer, the cells were added with PerCP-labeled anti-human IFN-γ antibody, and incubated for 30 minutes at 4° C. The cells were washed with Perm./Wash Buffer and analyzed by FACS.
Thawing, Seeding and Subculturing of B-LCL Cell as Feeder Cell
Cryopreserved cells were thawed and started to be cultured at $3 \times 10$ cells/well, and then subcultured at the time of subconfluent. The B-LCL cells thus obtained were used as feeder cells for PHA stimulation.
Isolation of $CD4^+$ Cells by MACS
According to a manufacturer's recommendation protocol, $CD4^+$ cells were isolated by positive selection from the cultured cells using MACS Microbeads.
Cloning and Amplification of WT1-332-Specific Th1 Cell by Limiting Dilution
The feeder B-LCL cells and PBMCs ($3 \times 10^6$/mL or less) were treated with mitomycin C solution (final concentration=50 μg/mL) for 45 minutes in a $CO_2$ incubator. After washed with AIM-V, two types of B-LCL cells and two types of PBMCs, 4 types of cells in total, were mixed (final concentration: $2.5 \times 10^5$ cells/mL for PBMC and $2.5 \times 10^4$ cells/well for B-LCL cell/ml). A set of the mixtures was prepared according to the number of the samples to be cloned, and PHA was added at a final concentration 200 ng/mL to make a PHA containing feeder cell liquid mixture.
Next, from the fractionated $CD4^+$ cell samples, samples showing a high $CD4^+IFN-γ^-$ cell ratio in ICS were selected, and the $CD4^+$ cell concentration was adjusted to 10 cells/ml with the PHA containing feeder cell liquid mixture thus prepared, and the cells were seeded on a 96 well plate at 100 μL/well (total number of PBMCs: $5.0 \times 10^4$ cells/well; B-LCL cells: $5.0 \times 10^3$ cells/well; PHA: 200 ng/mL; CD4 cells: one cell/well) and started to be cultured. Five days later, an equal amount of 80 U/mL IL-2 containing medium was added to the culture medium, and after that, half of the medium was changed with 80 U/mL IL-2 containing medium every other day. During the culture, cells in a well showing clear amplification were scaled up to 48 well plates, and continued to be cultured.

On day 10 from the start of cloning and after that at intervals of 14 days, PHA stimulation was applied for amplification as described above except that the culture plate, the total number of PBMCs, the total number of B-LCL cells, PHA final concentration, and the number of Th1 clone cells to be amplified were changed to 24 well plate, $1.0 \times 10^6$ cells/well, $1.0 \times 10^5$ cells/well, 50 ng/ml, and $2.0 \times 10^5$ cells/well or less, respectively. Also, IL-2 was added on day 3 from the start of culture, and the IL-2 concentration of the medium to be further added was set to 200 U/mL.

Peptide Stimulation of Th1 Clone Cell

To check the antigen reactivity of Th1 clone cells which had been cloned and amplified, the collected Th1 clone cells were seeded onto 96 well round-bottom plates in one well or three wells. To the wells, 10 μM acetic acid or 20 μg/mL of peptide was added, and culture was started (the total amount of medium: 200 μL/well). Culture supernatants were collected after about 24 hours.

ELISA

The IFN-γ concentration in each culture supernatant was measured after the culture supernatant was diluted 4 times with Assay Diluent (Becton Dickinson). The IFN-γ concentration was measured using BD OptEIA ELISA set (human IFN-γ, Becton Dickinson) according to the manufacture's protocol except that the antibody was diluted 500 times, the range of the calibration curve was changed to 18.75-1200 μg/mL, and the chromogenic reaction time was changed to 5 minutes. Also, an extrapolation value was used when a measured value exceeded the measurement range, and the measured value was regarded as 0 when the absorbance was less than 0.

Preparation of Th1 Clone Cell Master Cell Bank

Th1 clone cells of which antigen reactivity was confirmed were cryopreserved in cell banker, and used as master cell banks.

Evaluation

To evaluate whether WT1-332-specific Th1 cells were significantly induced in the CD4+ cells cultured for 14 days under the WT1-332 stimulus, WT1-332-specific Th1 cell ratio (%) and WT1-332-nonspecific Th1 cell ratio (%) were calculated according to the following formulae.

WT1-332-specific Th1 cell ratio (%)=number of CD4+, intracellular IFN-γ+ cells with WT1-332 stimulation/total number of viable cells×CD4+ cell ratio after fractionation/CD4+ cell ratio before fractionation×100

WT1-332-nonspecific Th1 cell ratio (%)=number of CD4+, intracellular IFN-γ+ cells with AcOH stimulation/total number of viable cells×100× CD4+ cell ratio after fractionation/CD4+ cell ratio before fractionation×100

Cloning was carried out in 6 to 7 samples for which the value obtained by subtracting the WT1-332-nonspecific Th1 ratio from the WT1-332-specific Th1 ratio was high.

The IFN-γ concentration of culture supernatant of each group was measured by ELISA, and when the IFN-γ production upon WT1-332 addition was higher than that upon solvent addition 500 μg/mL or more and 1.2 times or more, the groups were considered to maintain the antigen reactivity and used in subsequent experiments.

(3) Results

Various Th1 clone cells were established. It was confirmed as a result of typing that some of the obtained clones had new restricted alleles. The results were shown in Table 4. In Example 2, using those clones, it was determined whether WT1-332 could activate Th1 cells in a manner restricted to specific HLA types.

TABLE 4

| Clone ID | Clone Names | HLA Type | | | | | |
|---|---|---|---|---|---|---|---|
| | | DRB1 | | DPB1 | | DQB1 | |
| CloneR82-1 | #147-2F1 | 08:02 | 14:03 | 02:01 | 02:01 | 03:01 | 03:02 |
| CloneR132-1 | #142-2D7 | 01:01 | 13:02 | 04:01 | 04:02 | N.T. | N.T. |
| CloneR143-1 | #61-3F9 | 14:03 | 15:02 | 02:01 | 03:01 | N.T. | N.T. |
| CloneR145-2 | #77-3H6 | 04:05 | 14:05 | 05:01 | 05:01 | N.T. | N.T. |
| CloneQ32-1 | #147-2G6 | 08:02 | 14:03 | 02:01 | 02:01 | 03:01 | 03:02 |
| CloneQ41-2 | #106-1H11 | 04:05 | 15:01 | 05:01 | 05:01 | 04:01 | 06:02 |

*Underline shows new restricted alleles.
*N.T. means that HLA typing was not performed for the HLA type.

Example 2: Determination of Restricted Allele of Established WT1-332-Specific Th1 Clone Cell Using the WT1-332-specific Th1 clone cells established in Example 1 (referred to as "the Th1 clone cells" hereinafter), it was determined whether WT1-332 could activate Th1 cells in a manner restricted to specific HLA types and the restricted alleles were confirmed.

(1) Test Compound
B-LCL Cell Line

TABLE 5-1

Antigen presenting B-LCL cells for DRB1*08:02 restriction analysis

| Feature of HLA | B-LCL | HLA type | | | | | | | |
|---|---|---|---|---|---|---|---|---|---|
| | | DRB1 | | DPB1 | | DQB1 | | DRB3, 4, 5 | |
| DRB1*08:02 (+) | HEV#0052 | 08:02 | 14:03 | 05:01 | 05:01 | 03:02 | 03:01 | blank | B3*01:01 |
| DRB1*08:02 (+) | HEV#0324 | 08:02 | 15:02 | 04:02 | 09:01 | 04:02 | 06:01 | blank | B5*01:02 |
| DRB1*08:02 (−) | HEV#0042 | 04:05 | 13:01 | 05:01 | 05:01 | 04:01 | 06:03 | B4*01:03 | B3*01:01 |
| DRB1*08:02 (−) | HEV#0238 | 04:06 | 12:01 | 05:01 | 02:01 | 03:01 | 03:02 | B3*02:02 | B4*01:03 |
| DRB1*08:02 (−) | HEV#0013 | 04:05 | 11:01 | 02:01 | 05:01 | 03:01 | 04:01 | B4*01:03 | B3*02:02 |
| DRB1*08:02 (−) | HEV#0057 | 09:01 | 09:01 | 02:01 | 09:01 | 03:03 | 03:03 | B4*01:03 | B4*01:03 |

TABLE 5-2

Antigen presenting B-LCL cells for DRB1*13:02 restriction analysis

| Feature of HLA | B-LCL | DRB1 | | DPB1 | | DQB1 | | DRB3, 4, 5 | |
|---|---|---|---|---|---|---|---|---|---|
| DRB1*13:02 (−) | HEV#0201 | 01:01 | 04:05 | 04:02 | 05:01 | 03:03 | 05:01 | B4*01:03 | blank |
| DRB1*13:02 (−) | HEV#0073 | 01:01 | 09:01 | 04:02 | 05:01 | 03:03 | 05:01 | B4*01:03 | blank |
| DRB1*13:02 (−) | HEV#0271 | 09:01 | 09:01 | 04:02 | 05:01 | 03:03 | 03:03 | B4*01:03 | B4*01:03 |
| DRB1*13:02 (−) | 1333-8272 | 08:01 | 10:01 | 04:01 | 02:01 | 04:02 | 05:01 | blank | blank |
| DRB1*13:02 (+) | HEV#0046 | 04:01 | 13:02 | 04:01 | 05:01 | 03:01 | 06:04 | B4*01:02 | B3*03:01 |
| DRB1*13:02 (−) | HEV#0038 | 04:01 | 12:02 | 04:01 | 05:01 | 03:01 | 03:01 | B4*01:02 | B3*03:01 |
| DRB1*13:02 (−) | HEV#0110 | 04:01 | 04:03 | 02:01 | 05:01 | 03:01 | 03:02 | B4*01:03 | B4*01:02 |
| DRB1*13:02 (−) | HEV#0024 | 04:10 | 12:02 | 13:01 | 05:01 | 03:01 | 04:02 | B4*01:03 | B3*03:01 |
| DRB1*13:02 (−) | HEV#0342 | 09:01 | 08:03 | 14:01 | 05:01 | 03:01 | 03:03 | B4*01:03 | blank |

TABLE 5-3

Antigen presenting B-LCL cells for DRB1*14:03 restriction analysis

| Feature of HLA | B-LCL | DRB1 | | DPB1 | | DQB1 | | DRB3, 4, 5 | |
|---|---|---|---|---|---|---|---|---|---|
| DRB1*14:03 (−) | HEV#0052 | 08:02 | 14:03 | 05:01 | 05:01 | 03:02 | 03:01 | blank | B3*01:01 |
| DRB1*14:03 (−) | HEV#0324 | 08:02 | 15:02 | 04:02 | 09:01 | 04:02 | 06:01 | blank | B5*01:02 |
| DRB1*14:03 (−) | HEV#0042 | 04:05 | 13:01 | 05:01 | 05:01 | 04:01 | 06:03 | B4*01:03 | B3*01:01 |
| DRB1*14:03 (−) | HEV#0238 | 04:06 | 12:01 | 05:01 | 02:01 | 03:01 | 03:02 | B3*02:02 | B4*01:03 |
| DRB1*14:03 (−) | HEV#0035 | 04:05 | 15:02 | 05:01 | 09:01 | 04:02 | 06:01 | B4*01:03 | B5*01:02 |
| DRB1*14:03 (+) | HEV#0012 | 04:05 | 08:03 | 05:01 | 05:01 | 04:01 | 06:01 | B4*01:03 | blank |
| DRB1*14:03 (−) | HEV#0057 | 09:01 | 09:01 | 02:01 | 09:01 | 03:03 | 03:03 | B4*01:03 | B4*01:03 |
| DRB1*14:03 (−) | HEV#0013 | 04:05 | 11:01 | 02:01 | 05:01 | 03:01 | 04:01 | B4*01:03 | B3*02:02 |
| DRB1*14:03 (−) | HEV#0342 | 09:01 | 08:03 | 14:01 | 05:01 | 03:01 | 03:03 | B4*01:03 | blank |
| DRB1*14:03 (−) | HEV#0050 | 04:05 | 15:02 | 03:01 | 09:01 | 04:01 | 06:01 | B4*01:03 | B5*01:02 |

TABLE 5-4

Antigen presenting B-LCL cells for DRB1*14:05 restriction analysis

| Feature of HLA | B-LCL | DRB1 | | DPB1 | | DQB1 | | DRB3, 4, 5 | |
|---|---|---|---|---|---|---|---|---|---|
| DRB1*14:05 (−) | HEV#0201 | 01:01 | 04:05 | 04:02 | 05:01 | 03:03 | 05:01 | B4*01:03 | blank |
| DRB1*14:05 (−) | HEV#0073 | 01:01 | 09:01 | 04:02 | 05:01 | 03:03 | 05:01 | B4*01:03 | blank |
| DRB1*14:05 (+) | ISH5 | 09:01 | 14:05 | 05:01 | 05:01 | 03:03 | 03:03 | B3*02:02 | B4*01:03 |
| DRB1*14:05 (−) | HEV#0271 | 09:01 | 09:01 | 05:01 | 04:02 | 03:03 | 03:03 | B4*01:03 | B4*01:03 |
| DRB1*14:05 (−) | HEV#0058 | 14:06 | 13:02 | 04:01 | 05:01 | 03:01 | 06:04 | B3*03:01 | B3*02:02 |
| DRB1*14:05 (−) | HEV#0055 | 08:03 | 14:01 | 04:02 | 05:01 | 05:03 | 06:01 | B3*02:02 | blank |
| DRB1*14:05 (−) | HEV#0035 | 04:05 | 15:02 | 05:01 | 09:01 | 04:01 | 06:01 | B4*01:03 | B5*01:02 |
| DRB1*14:05 (−) | HEV#0050 | 04:05 | 15:02 | 03:01 | 09:01 | 04:01 | 06:01 | B4*01:03 | B5*02:02 |

TABLE 5-5

Antigen presenting B-LCL cells for DQB1*03:02 restriction analysis

| Feature of HLA | B-LCL | DRB1 | | DPB1 | | DQB1 | | DRB3, 4, 5 | |
|---|---|---|---|---|---|---|---|---|---|
| DBQ1*03:02 (+) | HEV#0052 | 08:02 | 14:03 | 05:01 | 05:01 | 03:02 | 03:01 | blank | B3*01:01 |
| DBQ1*03:02 (−) | HEV#0324 | 08:02 | 15:02 | 04:02 | 09:01 | 04:02 | 06:01 | blank | B5*01:02 |
| DBQ1*03:02 (+) | HEV#0238 | 04:06 | 12:01 | 05:01 | 02:01 | 03:01 | 03:02 | B3*02:02 | B4*01:03 |
| DBQ1*03:02 (−) | HEV#0042 | 04:05 | 13:01 | 05:01 | 05:01 | 04:01 | 06:03 | B4*01:03 | B3*01:01 |
| DBQ1*03:02 (−) | HEV#0013 | 04:05 | 11:01 | 02:01 | 05:01 | 03:01 | 04:01 | B4*03:01 | B3*02:02 |

TABLE 5-6

Antigen presenting B-LCL cells for DQB1*04:01 restriction analysis

| Feature of HLA | B-LCL | DRB1 | | DPB1 | | DQB1 | | DRB3, 4, 5 | |
|---|---|---|---|---|---|---|---|---|---|
| DQB1*04:01 (−) | HEV#0201 | 01:01 | 04:05 | 04:02 | 05:01 | 03:03 | 05:01 | B4*01:03 | blank |
| DQB1*04:01 (−) | HEV#0073 | 01:01 | 09:01 | 04:02 | 05:01 | 03:03 | 05:01 | B4*01:03 | blank |
| DQB1*04:01 (+) | HEV#0174 | 04:05 | 15:01 | 05:01 | 05:01 | 04:01 | 06:02 | B4*01:03 | B5*01:01 |
| DQB1*04:01 (+) | HEV#0013 | 04:05 | 11:01 | 02:01 | 05:01 | 03:01 | 04:01 | B4*01:03 | B3*02:02 |
| DQB1*04:01 (+) | HEV#0035 | 04:05 | 15:02 | 05:01 | 09:01 | 04:01 | 06:01 | B4*01:03 | B5*01:02 |
| DQB1*04:01 (+) | HEV#0050 | 04:05 | 15:02 | 03:01 | 09:01 | 04:01 | 06:01 | B4*01:03 | B5*01:02 |

(2) Test Method

Preparation of Medium

Human AB Serum and FBS were used after inactivation and filtration through a 0.2 μm filter. Twenty U/mL heparin HBSS, RPMI-1640 containing 10% FBS and 1% P/S (100 units/mL penicillin, 100 μg/mL streptomycin), and AIM-V (Invitrogen) containing 10% human AB serum were used for PBMC separation, B-LCL cell culture, and other culture, respectively. Cell culture was performed in a 37° C.-5% $CO_2$ incubator in each medium.

Experimentation Method

HLA restriction of Th1 clone cells was determined by using WT1-332-pulsed B-LCL cells having an appropriate allele as antigen presenting cells and measuring the amount of IFN-γ produced.

Specifically, Th1 clone cells were cultured under the PHA stimulus using the feeder B-LCL cells and xenogeneic PBMCs prepared from peripheral blood as feeder cells. Next, B-LCL cells treated with WT1-332 or solvent were used as antigen presenting cells and cultured with the collected Th1 clone cells. The amount of IFN-γ produced was measured to determine whether WT1-332-specific antigen stimulus was present. Based on the HLA class II types of each Th1 clone, B-LCL cells having some different HLA types were used as antigen presenting cells, and thereby HLA class II restriction of the Th1 clone was determined.

Thawing and Seeding of B-LCL Cell as Feeder Cell

Cryopreserved cells were thawed on day 0 and started to be cultured at $1 \times 10^5$ cells/well. The cells were collected on day 3 and used as feeder cells for PHA stimulation.

Preparation of PBMC

PBMCs were prepared by density centrifugation from peripheral blood of healthy volunteers by day 2. After the cell number was counted, cell pellets were collected and re-suspended in cell banker (Mitsubishi Chemical Medience Corporation), and then dispensed into cryotubes to be cryopreserved in a freezer set at −80° C. At the time of PHA stimulation, the cryopreserved cells were thawed and provided as the feeder PBMCs.

Thawing and Seeding of Th1 Clone Cell

On day 2, cryopreserved cells were thawed and started to be cultured at $2 \times 10^6$ cells/well or less in 20 U/mL IL-2 containing medium. The cells were collected on day 3 and used as Th1 clone cells for PHA stimulation.

PHA Stimulation of Th1 Clone Cell

On day 3, the feeder B-LCL cells and PBMCs were treated with mitomycin C solution (final concentration=50 g/mL) for 45 minutes in a $CO_2$ incubator. After washed with AIM-V, two types of PBMCs and two types of B-LCL cells, 4 types of cells in total, were mixed (final concentration: $1.0 \times 10^6$ cells/mL for PBMC and $1.0 \times 10^5$ cells/well for B-LCL cell/ml). A set of the mixtures was prepared according to the number of Th1 clone cells to be seeded, and PHA was added at a final concentration 100 ng/mL to make a PHA containing feeder cell liquid mixture. Next, the cultured Th1 clone cells were seeded on 24 well plates at 0.5 mL/well (cell concentration $4.0 \times 10^5$ cells/mL), and further added with the PHA containing feeder cell liquid admixture at 0.5 mL/well, and the cells were cultured. On day 6, an equal amount of 200 U/mL IL-2 containing medium was added to the culture medium, and on day 8, day 10, day 12, and day 14, half of the medium was changed with 40 U/mL IL-2 containing medium. On day 15, the cells were used for the restriction analysis. When the cells reached confluent during the culture, the cells were subcultured using 20 U/mL IL-2 containing medium.

Thawing and Seeding of B-LCL Cell as Antigen Presenting Cell for Restriction Analysis On day 11, cryopreserved cells were thawed and started to be cultured at about $1 \times 10^1$ cells/well. The cells were collected on day 15 and used for the restriction analysis.

Restriction Analysis

Th1 clone cells were collected on day 15, and seeded on 96 well round-bottom plates according to the number of the collected cells at $1.0$-$2.5 \times 10^4$ cells/100 μL/well in 3 wells. B-LCL cells as antigen presenting cells adjusted to $1 \times 10^6$ cells/mL were dispensed into two conical tubes in 4-7 mL, and one was added with acetic acid at a final concentration of 10 μM and another was added with WT1-332 at a final concentration of 20 μg/ml. After 2 hours culture, the cells were washed with AIM-V and added to the 96 well plates onto which Th1 clone cells were seeded at $2.5 \times 10^4$ cells/100 μL/well and then cultured for 16 hours or more. To confirm the WT1-332 reactivity, wells added with WT1-332 or solvent instead of B-LCL cells were prepared in the same plate.

ELISA

The IFN-γ concentration in each culture supernatant was measured after the culture supernatant was diluted 100 times with Assay Diluent (Becton Dickinson). The IFN-γ concentration was measured using BD OptEIA ELISA set (human IFN-γ, Becton Dickinson) according to the manufacture's protocol except that the range of the calibration curve was changed to 5-640 μg/mL, and the chromogenic reaction time was changed to 10 minutes. Also, an extrapolation value was used when a measured value exceeded the measurement range, and the measured value was regarded as 0 when the absorbance was less than 0.

Evaluation

The amount of IFN-γ in each culture supernatant.

(3) Results (i) HLA Restriction Analysis of Th1 Clone Cell CloneR82-1 (DRB1*08:02/14:03, DPB1*02:01, DQB1*03:01/03:02)

The IFN-γ production of CloneR82-1 was detected by the stimulation with WT1-332-pulsed DRB1*08:02(+) B-LCLs (HEV#0052 and HEV#0324) (FIG. 1). Therefore, CloneR82-1 was revealed to be a WT1-332-specific HLA-DRB1*08:02-restricted Th1 clone.

(ii) HLA Restriction Analysis of Th1 Clone Cell CloneR132-1 (DRB1*01:01/13:02, DPB1*04:01/04:02)

Figure 2:
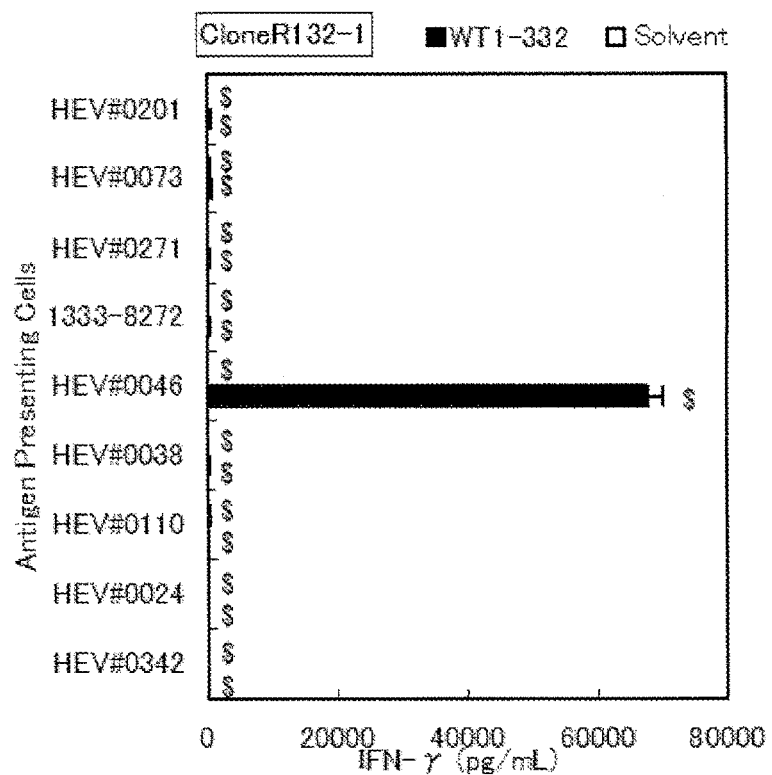
FIG. 2 shows HLA restriction of Clone R132-1. The horizontal axis shows the amount of IFN-γ production (pg/ml) upon addition of WT1-332 (black column) or solvent (white column). The vertical axis shows types of antigen presenting B-LCL cells. Data represent mean±SD (triplicates). $: Data include extrapolated value(s).

The IFN-γ production of CloneR132-1 was detected by the stimulation with WT1-332-pulsed DRB1*13:02(+) B-LCL (HEV#0046) (FIG. 2). Therefore, CloneR132-1 was revealed to be a WT1-332-specific HLA-DRB1*13:02-restricted Th1 clone.

(iii) HLA Restriction Analysis of Th1 Clone Cell CloneR143-1 (DRB1*14:03/15:02, DPB1*02:01/03:01)

Figure 3:
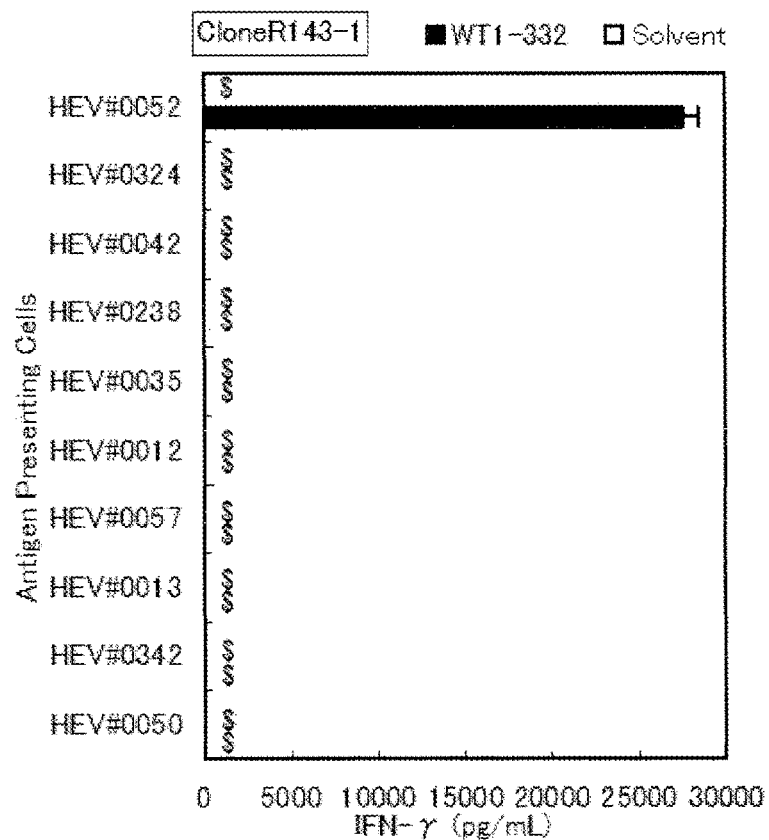
FIG. 3 shows HLA restriction of Clone R143-1. The horizontal axis shows the amount of IFN-γ production (pg/ml) upon addition of WT1-332 (black column) or solvent (white column). The vertical axis shows types of antigen presenting B-LCL cells. Data represent mean±SD (triplicates). $: Data include extrapolated value(s).

The IFN-γ production of CloneR143-1 was detected by the stimulation with WT1-332-pulsed DRB1*14:03(+) B-LCL (HEV#0052) (FIG. 3). Therefore, CloneR132-1 was revealed to be a WT1-332-specific HLA-DRB1*14:03-restricted Th1 clone.

(iv) HLA Restriction Analysis of Th1 Clone Cell CloneR145-2 (DRB1*04:05/14:05, DPB1*05:01)

Figure 4:
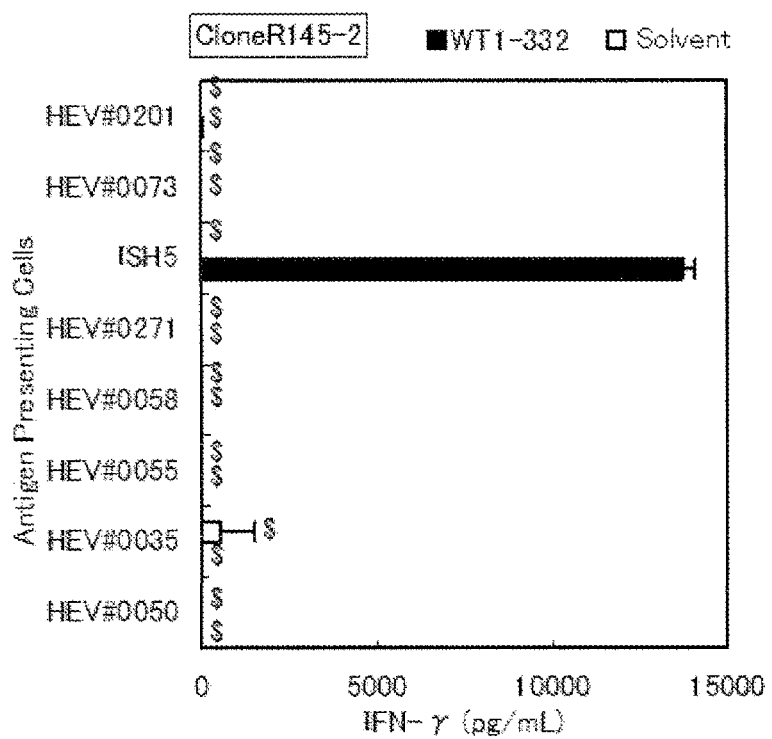
FIG. 4 shows HLA restriction of Clone R145-2. The horizontal axis shows the amount of IFN-γ production (pg/ml) upon addition of WT1-332 (black column) or solvent (white column). The vertical axis shows types of antigen presenting B-LCL cells. Data represent mean±SD (triplicates). $: Data include extrapolated value(s).

The IFN-γ production of CloneR145-2 was detected by the stimulation with WT1-332-pulsed DRB1*14:05(+) B-LCL (ISH5) (FIG. 4). Therefore, Clone R145-2 was revealed to be a WT1-332-specific HLA-DRB1*14:05-restricted Th1 clone.

(v) HLA Restriction Analysis of Th1 Clone Cell CloneQ32-1 (DRB1*08:02/14:03, DPB1*02:01, DQB1*03:01/03:02)

Figure 5:
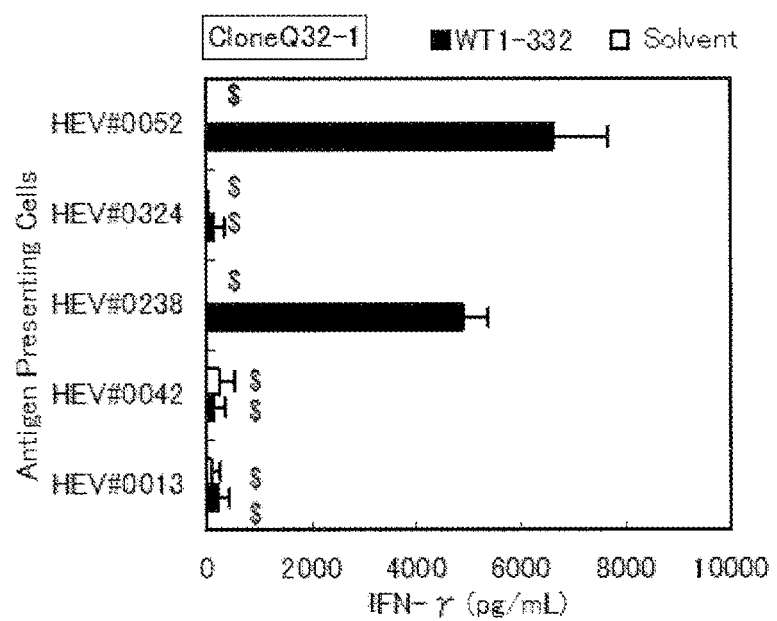
FIG. 5 shows HLA restriction of Clone Q32-1. The horizontal axis shows the amount of IFN-γ production (pg/ml) upon addition of WT1-332 (black column) or solvent (white column). The vertical axis shows types of antigen presenting B-LCL cells. Data represent mean±SD (triplicates). $: Data include extrapolated value(s).

The IFN-γ production of CloneQ32-1 was detected by the stimulation with WT1-332-pulsed DQB1*03:02(+) B-LCLs (HEV#0052 and HEV#0238) (FIG. 5). Therefore, CloneQ32-1 was revealed to be a WT1-332-specific HLA-DQB1*03:02-restricted Th1 clone.

(vi) HLA Restriction Analysis of Th1 Clone Cell CloneQ41-1 (DRB1*04:05/15:01, DPB1*05:01, DQB1*04:01/06:02)

Figure 6:
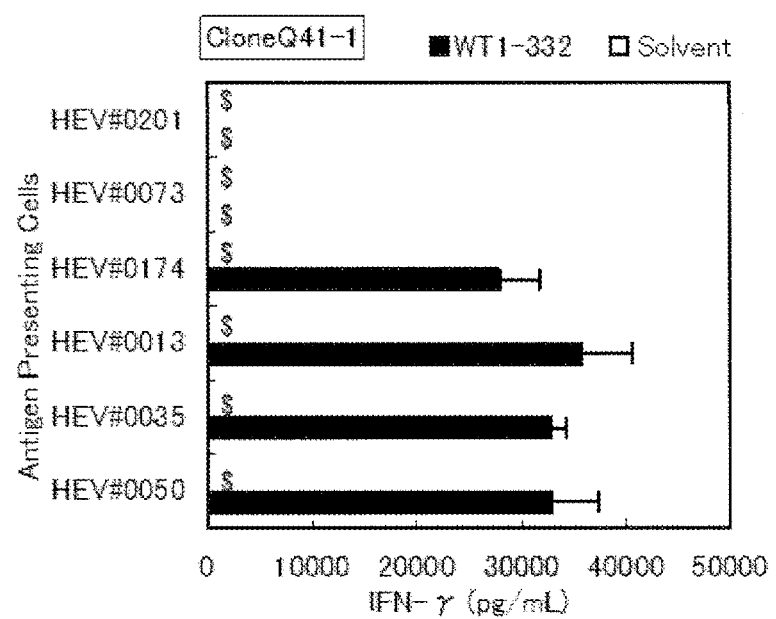
FIG. 6 shows HLA restriction of Clone Q41-1. The horizontal axis shows the amount of IFN-γ production (pg/ml) upon addition of WT1-332 (black column) or solvent (white column). The vertical axis shows types of antigen presenting B-LCL cells. Data represent mean±SD (triplicates). $: Data include extrapolated value(s).

The IFN-γ production of CloneQ41-1 was detected by the stimulation with various antigen presenting cells pulsed with WT1-332 (HEV#0174, HEV#0013, HEV#0035, and HEV#0050), but not with WT1-332-pulsed HEV#0201 and HEV#0073 (FIG. 6). DQB1*04:01 was only expressed in HEV#0174, HEV#0013, HEV#0035, and HEV#0050. Therefore, CloneQ41-1 was revealed to be a WT1-332-specific DQB1*04:01-restricted Th1 clone.

INDUSTRIAL APPLICABILITY

The present invention provides a method for activating helper T cells and/or cytotoxic T cells using a WT1 peptide having the ability to bind to an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule and a composition therefor, a pharmaceutical composition for treating and/or preventing a cancer by activating helper T cells and/or cytotoxic T cells, and the like. Thus, the present invention is applicable to the field of pharmaceuticals and the like, for example, development and production fields of preventives or remedies for various hematopoietic organ tumors and solid cancer highly expressing a WT1 gene.

SEQUENCE LISTING FREE TEXT

SEQ ID NO: 2: Synthetic peptide

The invention claimed is:

1. A method for activating helper T cells, comprising activating helper T cells by adding a WT1 peptide to antigen presenting cells, wherein the helper T cells recognize a complex of the WT1 peptide and an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, wherein the WT1 peptide consists of:

(a) the amino acid sequence depicted in SEQ ID NO: 2; or (b) an amino acid sequence in which one amino acid is substituted, deleted, or added in the amino acid sequence depicted in SEQ ID NO: 2; and wherein the WT1 peptide is capable of binding to the MHC class II molecule.

2. A method for activating cytotoxic T cells, comprising administering a WT1 peptide, a polynucleotide encoding the WT1 peptide, an expression vector containing the polynucleotide, or cells containing the expression vector to a subject having an MHC class II molecule selected from an HLA-DRB1*08:02 molecule, an HLA-DRB113:02 molecule, an HLA-DRB1*14:03 molecule, an HLA-DRB1*14:05 molecule, an HLA-DQB1*03:02 molecule, and an HLA-DQB1*04:01 molecule, wherein the WT1 peptide consists of:

(a) the amino acid sequence depicted in SEQ ID NO: 2; or (b) an amino acid sequence in which one amino acid is substituted, deleted, or added in the amino acid sequence depicted in SEQ ID NO: 2; and wherein the WT1 peptide is capable of binding to the MHC class II molecule.

3. A method comprising administering a WT1 peptide, a polynucleotide encoding the WT1 peptide, an expression vector containing the polynucleotide, or cells containing the expression vector to a subject who has been diagnosed with cancer and has an MHC class II molecule selected from an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule, wherein the WT1 peptide consists of:

(a) the amino acid sequence depicted in SEQ ID NO: 2; or (b) an amino acid sequence in which one amino acid is substituted, deleted, or added in the amino acid sequence depicted in SEQ ID NO: 2; and wherein the WT1 peptide is capable of binding to the MHC class II molecule.

4. The method according to claim 2 or claim 3, comprising administering the WT1 peptide to the subject.

5. The method according to claim 4, wherein the WT1 peptide consists of: Lys Arg Tyr Phe Lys Leu Ser His Leu Gln Met His Ser Arg Lys His (SEQ ID NO:2).

6. The method according to claim 1, wherein the addition of the WT1 peptide to antigen presenting cells is carried out by contacting the antigen presenting cells with the WT1 peptide, or introducing a polynucleotide encoding the WT1 peptide or an expression vector containing the polynucleotide into the antigen presenting cells.

7. The method according to claim 1, which comprises administering the WT1 peptide a subject having an MHC class II molecule selected from the group consisting of: an HLA-DRB1*08:02 molecule, an HLA-DRB1*13:02 molecule, an HLA-DRB1*14:03 molecule, an HLA-DRB1*14:05 molecule, an HLA-DQB1*03:02 molecule, and an HLA-DQB1*04:01 molecule.

8. The method according to claim 7, wherein the WT1 peptide consists of: Lys Arg Tyr Phe Lys Leu Ser His Leu Gln Met His Ser Arg Lys His (SEQ ID NO:2).

9. The method according to claim 3, wherein the MHC class II molecule is selected from an HLA-DRB1*08:02 molecule, an HLA-DRB1*14:03 molecule, an HLA-DRB1*14:05 molecule, an HLA-DQB1*03:02 molecule, and an HLA-DQB1*04:01 molecule.

* * * * *

UNITED STATES PATENT AND TRADEMARK OFFICE
CERTIFICATE OF CORRECTION

PATENT NO. : 9,833,493 B2
APPLICATION NO. : 14/652298
DATED : December 5, 2017
INVENTOR(S) : Hiroshi Kubo et al.

It is certified that error appears in the above-identified patent and that said Letters Patent is hereby corrected as shown below:

On the Title Page

Item (73), Assignee: "International Institute of Cancer Immunology, Inc., Osaka (JP)" should read --International Institute of Cancer Immunology, Inc., Osaka (JP); Otsuka Pharmaceutical Co., Ltd., Tokyo (JP)--

Signed and Sealed this
Sixteenth Day of October, 2018

Andrei Iancu
*Director of the United States Patent and Trademark Office*